(12) United States Patent
Tribouley

(10) Patent No.: US 6,297,367 B1
(45) Date of Patent: Oct. 2, 2001

(54) POLYNUCLEOTIDE ENCODING TNFL1

(75) Inventor: Catherine Tribouley, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/286,529

(22) Filed: Apr. 5, 1999

Related U.S. Application Data

(63) Continuation-in-part of application No. 09/212,270, filed on Dec. 16, 1998.
(60) Provisional application No. 60/068,959, filed on Dec. 30, 1997.

(51) Int. Cl.$^7$ .................................................. C07H 21/04
(52) U.S. Cl. .................. 536/23.5; 435/320.1; 435/252.3; 435/69.1; 530/350
(58) Field of Search ........................... 530/350; 536/23.5; 535/370.1, 252.3, 69.1

(56) References Cited

FOREIGN PATENT DOCUMENTS

| | | |
|---|---|---|
| 869 180 A1 | 10/1998 | (EP) . |
| WO 94/01548 * | 1/1994 | (WO) . |
| WO 97/33902 | 9/1997 | (WO) . |
| WO 98/18921 | 5/1998 | (WO) . |
| WO 98/27114 | 6/1998 | (WO) . |
| WO 98/55620 | 12/1998 | (WO) . |
| WO 98/55621 | 12/1998 | (WO) . |
| WO 99/11791 | 3/1999 | (WO) . |
| WO 99/12964 | 3/1999 | (WO) . |

OTHER PUBLICATIONS

Hilllier et al., EST Database, Accession No. R16882, Apr. 1995.*

Hillier et al., EST Database, Accession No. AA682496. Zj18e08.s1 Soares_fetal_liver_spleen_1NFLS_S1 Homo sapiens cDNA clone Image:450662 3', mRNA sequence, Dec. 1997.*

Mukhopadhyay et al., "Identification and characterization of a novel cytokine, Thank, a TNF homologue that activates apoptosis, nuclear factor–κB, and c–Jun NH$_2$–terminal kinase," *The Journal of Biological Chemistry* 274(23):15978–15981, Jun. 4, 1999.

Schneider et al., "BAFF, a novel ligand of the tumor necrosis factor family, stimulates B cell growth," *J. Exp. Med.* 189(11):1747–1756, Jun. 7, 1999.

Tribouley et al., "Characterization of a new member of the TNF family expressed on antigen presenting cells," *Biol. Chem.* 380:1443–1447, Dec. 1999.

Database EMBL, ID No. AA682496, Accession No. AA682496, Dec. 10, 1997.

Aggarwal and Natarajan, "Tumor necrosis factors: Developments during the last decade," *Eur. Cytokine Netw.* 7(2): 93–124, Apr.–Jun. 1996.

Gruss, "Molecular, structural, and biological characteristics of the tumor necrosis factor ligand superfamily," *Int. J. Clin. Lab. Res.* 26: 143–159, 1996.

Gruss and Dower, "Tumor Necrosis Factor Ligand Superfamily: Involvement in the Pathology of Malignant Lymphomas," *Blood* 85(12): 3378–3404, 1995.

* cited by examiner

*Primary Examiner*—Lorraine Spector
*Assistant Examiner*—Eileen B. O'Hara
(74) *Attorney, Agent, or Firm*—Jane E. R. Potter; Kimberlin L. Morley; Robert P. Blackburn

(57) ABSTRACT

New members of the TNF and the TNFR superfamily of proteins have been identified. These proteins are promising targets for therapeutic intervention and mimesis. TNF-L and TNFR-L proteins can be used to induce cell death and/or proliferation of cells. Members of these superfamilies have been implicated in a broad variety of disease processes, making them central biological and physiological regulators.

6 Claims, 9 Drawing Sheets

1    MDDSTEREQSRLTSCLKKREEMKLKECVSILPRKESPSVRSSKDGKLLAATLLLALLSCC    60
61   LTVVSFYQVAALQGDLASLRAELQGHHAEKLPAGAGAPKAGLEEAPAVTAGLKIFEPPAP    120
121  GEGNSSQNSRNKRAVQGPEETVTQDCLQLIADSETPTIQKGSYTFVPWLLSFKRGSALEE    180
181  KENKILVKETGYFFIYGQVLYTDKTYAMGHLIQRKKVHVFGDELSLVTLFRCIQNMPETL    240
241  PNNSCYSAGIAKLEEGDELQLAIPRENAQISLDGDVTFFGALKLL    285

CONTROL    TNFL1

CONTROL    TNFL1

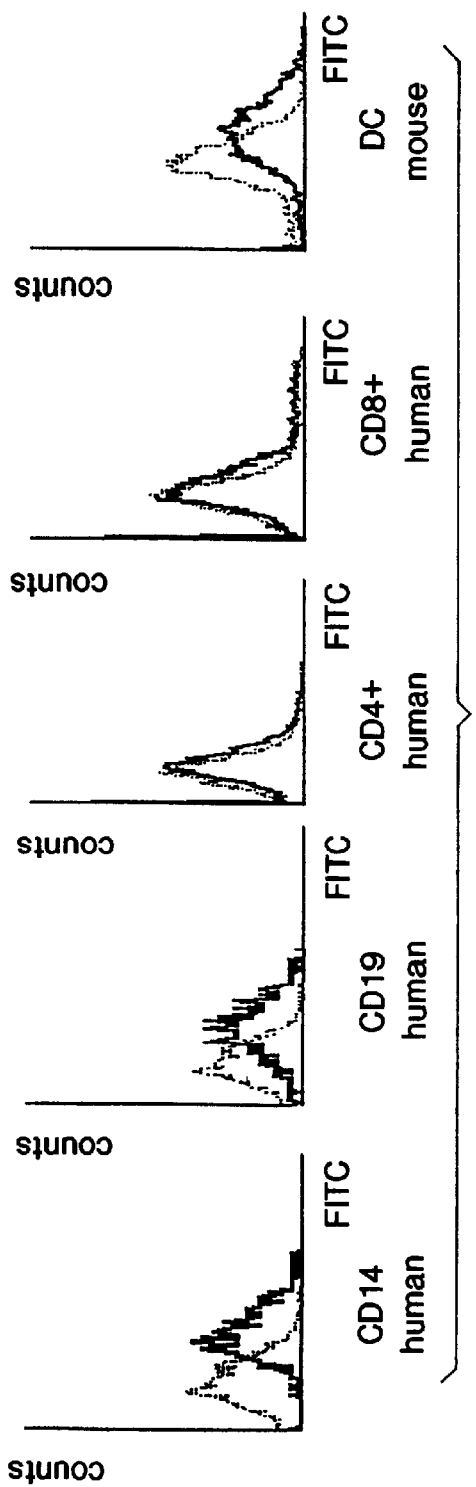
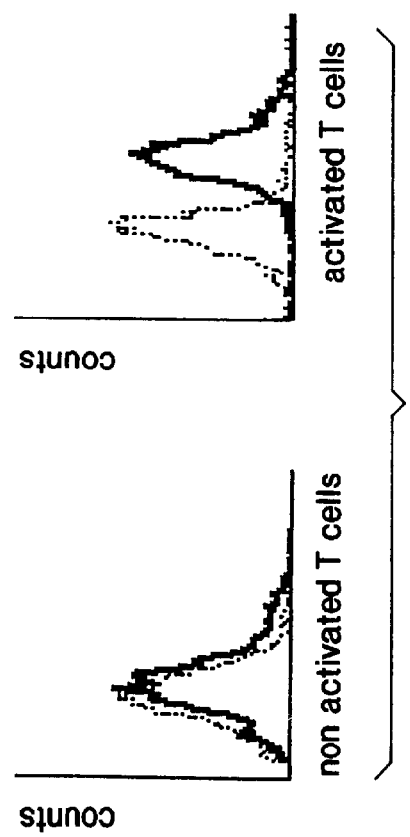
FIG. 4A
FIG. 4B

1   MDDSTEREQSRLTSCLKKREEMKLKECVSILPRKESPSVRSSKDGKLLAATLLALLSCC    60
61  LTVVSFYQVAALQGDLASLRAELQGHHAEKLPAGAGAPKAGLEEAPAVTAGL[KIFEPPAP  120
121 GEGNSSQNSRNKRAΨPGPEETVTQDCLQLIADSETPTIQKGSYTFVPWLLSFKRGSALEE   180
181 KENKILVKETGYFFIYGQVLYTDKTYAMGHLIQRKKVHVFGDELSLVTLFRCIQNMPETL   240
241 PNNSCYSAGIAKLEEGDELQLAIPRENAQISLDGDVTFFGALKLL                 285

POLYNUCLEOTIDE ENCODING TNFL1

CROSS-REFERENCE TO RELATED APPLICATIONS

This application claims the benefit of application Ser. No. 60/068,959 filed Dec. 30, 1997, and of application Ser. No. 09/212,270, filed Dec. 16, 1998, both of which are incorporated by reference herein.

BACKGROUND OF THE INVENTION

Tumor necrosis factor (TNF) is a pro-inflammatory cytokine which is produced by a wide spectrum of cells. It has a key role in host defense and immunosurveillance, mediating complex cellular responses. In excess, TNF may have detrimental effects.

Two specific, high affinity cell surface receptors, p55 TNF-R and p75 TNF-R, function as transducing elements, providing the intracellular signal for cell responses to TNF. While both types of TNF receptors are expressed by almost all cell types, the p75 receptor has been shown to be expressed primarily by cells of the immune system (B and T cells), cells of myeloid origin, and endothelial cells. Both receptors participate in the induction of NFκB and interleukin-6, in the generation of lymphocyte activated killer (LAK) cells, and in the proliferation of natural killer (NK) cells, as well as in anti-proliferation, cytotoxicity, and apoptosis.

TNF signaling to cells is largely mediated by the p55 TNF-R, while the main function of the p75 surface receptor is "ligand passing," i.e., TNF presentation to the p55 TNF-R. Presence of the cell surface p75 TNF receptor greatly enhances the rate of association of TNF to the p55 TNF receptor and may reverse the desensitization of p55 TNF-R to TNF. Pharmaceutical agents which affect p75 TNF-R may have a general impact on TNF function, including those activities in which the major signaling receptor is the p55 TNF-R.

The TNF-Rs also mediate many non-overlapping functions: the p55 receptor is involved in interleukin-2 receptor induction, anti-viral activities, growth stimulation, HLA antigen expression, and endothelial cell adhesion, while the p75 receptor mediates the TNF-induced thymocyte proliferation.

The p55 and p75 TNF-Rs are members of a superfamily which includes nerve growth factor receptor (NGFR), Fas antigen, CD27, CD30, CD40, OX40 and 4-1BB. The cysteine-rich domains of the extracellular part of these receptors are homologous to several viral proteins produced by cowpox virus, Shope fibroma virus, and the myxoma virus.

Because of the central role of TNF and its receptors in host defense and immunosurveillance, there is a need in the art to identify new members of the TNF and TNFR superfamilies.

SUMMARY OF THE INVENTION

It is an object of the invention to provide new members of the TNF and TNFR families, as well as methods of screening for compounds capable of modifying the activities of these proteins. This and other objects of the invention are provided by one or more of the embodiments described below.

One embodiment of the invention is an isolated human protein having an amino acid sequence which is at least 85% identical to an amino acid sequence selected from the group consisting of SEQ ID NOS:1, 2, 17 and 20. Percent identity is determined using a Smith-Waterman homology search algorithm using an affine gap search with a gap open penalty of 12 and a gap extension penalty of 1.

Another embodiment of the invention is a fusion protein comprising a first protein segment and a second protein segment fused together by means of a peptide bond. The first protein segment consists of a protein having an amino acid sequence selected from the group consisting of SEQ ID NOS:1, 2, 17 and 20.

Still another embodiment of the invention is a preparation of antibodies which specifically bind to a protein having an amino acid sequence selected from the group consisting of SEQ ID NOS: 1, 2, 17 and 20.

Even another embodiment of the invention is a cDNA molecule which encodes a protein having an amino acid sequence which is at least 85% identical to an amino acid sequence selected from the group consisting of SEQ ID NOS: 1, 2, 17 and 20. Percent identity is determined using a Smith-Waterman homology search algorithm using an affine gap search with a gap open penalty of 12 and a gap extension penalty of 1.

Yet another embodiment of the invention is a cDNA molecule which is at least 85% identical to a nucleotide sequence selected from the group consisting of SEQ ID NOS:6, 7, 18 and 19. Percent identity is determined using a Smith-Waterman homology search algorithm using an affine gap search with a gap open penalty of 12 and a gap extension penalty of 1.

A further embodiment of the invention is an isolated and purified subgenomic polynucleotide comprising a nucleotide sequence which hybridizes to a nucleotide sequence selected from the group consisting of SEQ ID NOS:6, 7, 18 and 19 after washing with 0.2×SSC at 65° C. The nucleotide sequence encodes a protein having an amino acid sequence selected from the group consisting of SEQ ID NOS: 1, 2, 17 and 20.

Another embodiment of the invention is a construct comprising a promoter and
a polynucleotide segment encoding an amino acid sequence selected from the group consisting of SEQ ID NOS: 1, 2, 17 and 20. The polynucleotide segment is located downstream from the promoter. Transcription of the polynucleotide segment initiates at the promoter.

Still another embodiment of the invention is a host cell comprising a construct which comprises a promoter and a polynucleotide segment encoding an amino acid sequence selected from the group consisting of SEQ ID NOS: 1, 2, 17 and 20.

Even another embodiment of the invention is a recombinant host cell comprising a new transcription initiation unit, wherein the new transcription initiation unit comprises in 5' to 3' order (a) an exogenous regulatory sequence, (b) an exogenous exon, and (c) a splice donor site. The new transcription initiation unit is located upstream of a coding sequence of a gene. The coding sequence is selected from the group consisting of SEQ ID NOS:6, 7, 18 and 19. The exogenous regulatory sequence controls transcription of the coding sequence of the gene.

Yet another embodiment of the invention is a method of screening for a compound capable of modulating cell death inducing activity of a protein. A first population of cells and a protein are incubated in the presence of a test compound. The protein comprises an amino acid sequence selected from the group of amino acid sequences shown in SEQ ID NOS: 1–5, 17 and 20. A second population of cells and the protein are incubated in the absence of a test compound. Viability of the first and second populations is determined. A test compound which increases or decreases viability of the first population relative to the second population is identified as capable of modulating the cell death inducing activity of the protein.

Even another embodiment of the invention is a method of identifying a binding partner of a first protein. A first protein is incubated with a second protein. The first protein comprises an amino acid sequence selected from the group consisting of SEQ ID NOS:1–5, 17 and 20. Formation of a complex between the first and second proteins is detected. Formation of the complex identifies the second protein as a binding partner of the first protein.

The present invention thus provides the art with the amino acid sequences of proteins which are new members of the TNF and TNFR families, as well as nucleotide sequences of polynucleotides which encode the proteins. These proteins and polynucleotides can be used to enhance or decrease TNF activities thereby providing therapeutic benefits, such as induction of cell death, lymphoid organogenesis, or host bacterial resistance, and inhibition of endotoxic shock, contact hypersensitivity, delayed type hypersensitivity, or immunocompetence of a transplant recipient. Methods of diagnosing neoplasia or predisposition to neoplasia are also provided. Proteins of the present invention are also useful for identifying compounds which can regulate the TNF-like or TNFR-like activities of these proteins.

BRIEF DESCRIPTION OF THE DRAWINGS

FIG. 1A shows the protein sequence of human TNFL1 (SEQ ID NO:1). The transmembrane domain is underlined. FIG. 1B shows alignments of the extracellular domains of several members of the TNF family (SEQ ID NO:22–25) with TNFL1 (SEQ ID NO:25). The conserved amino acids are boxed.

FIG. 3. FIG. 3 shows detection of TNFL1 expression using a purified polyclonal anti-peptide antibody.

FIG. 4. FIG. 4 shows flow cytometric analysis of the cell-surface expression of TNFL1 on sub-populations of human PBMCs and cultured cells.

FIG. 4A shows expression of TNFL1 on CD14+, CD19+, CD4+, and CD8+ human PBMCs and on mouse bone marrow-derived dendritic cells. Human PBMCs were stained with affinity purified D2710, followed by FITC-conjugated anti-rabbit IgG. They were subsequently stained with PE-conjugated CD14, CD19, CD4, or CD8. The histograms show TNFL1 expression (FITC) on PE-positive gated cells. The dotted lines represent the staining in the absence of primary antibody D2710.

FIG. 4B shows upregulation of TNFL1 surface expression on T cells after activation with anti-CD3 and anti-CD28 at 10 μg/ml in the presence of IL2 at 50 μg/ml for six days.

FIG. 5. FIG. 5 shows the effect of recombinant TNFL1 on activated T and B cells.

DETAILED DESCRIPTION OF THE INVENTION

Figures 2A, 2B:
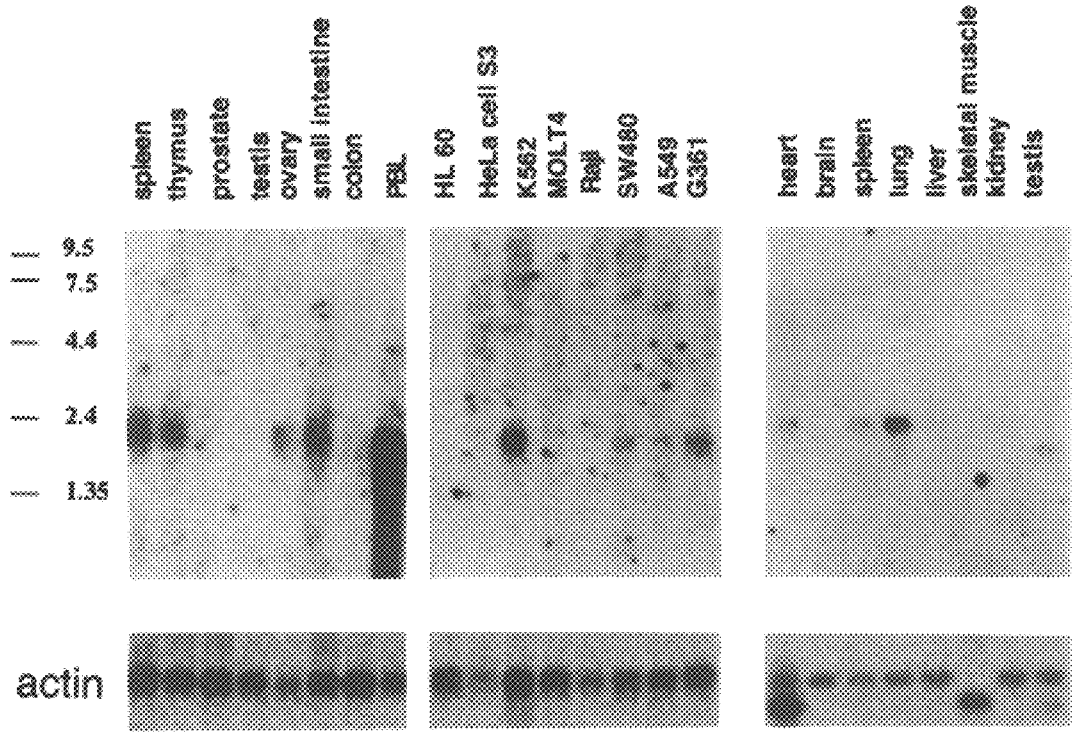
FIG. 2A shows TNFL1 mRNA expression in human tissues and cell lines.
FIG. 2B shows TNFL1 expression in mouse tissues. PBL, peripheral blood lymphocytes; HL60 promyelocytic leukemia HL60; HeLa, HeLa cell line S3; K562, chromic myelogenous leukemia K562; MOLT-4, lymphoblastic leukemia MOLT-4; Raji, Burkitt's lymphoma Raji; SW480, colorectal adenocarcinoma SW480; A549, lung carcinoma A549; G361, melanoma G361.

New members of the TNF and TNFR families are a discovery of the present invention. In particular, the present invention identifies two cDNA clones which encode new members of TNF ligand family and three cDNA clones which encode new members of TNFF family. Proteins and polynucleotides of the invention provide the art with diagnostic and therapeutic reagents as well as tools for discovering other therapeutic agents.

Two cDNA clones have been identified which show significant homology to members of TNF family. One cDNA clone (SEQ ID NO:6) was isolated from a human liver cDNA library. It encodes a protein designated as TNFL1

(SEQ ID NO:1), which has 27%–30% homology with TNF and 38% homology with lymphotoxin. TNFL1 contains a transmembrane domain. The TNFL1 cDNA clone encodes a 3 kb mRNA which can be detected in tissues associated with the immune system, such as peripheral blood lymphocytes, spleen, and thymus, as well as small intestine and ovary. TNFL1 protein is constitutively expressed on monocytes and B cells isolated from human peripheral blood lymphocytes, as well as on mouse dendritic cells and in mouse spleen. Expression of the protein can be up-regulated in natural killer cells. Activation of dendritic cells, for example with anti-CD4d antibody, can down-regulate expression of TNFL1 protein.

TNFL1 shares some common features with other members of the TNF family. TNFL1 is upregulated on activated T cells, as are TNF, Fas ligand, and CD30 ligand. TNFL1 induces activation of NFκB, which is also triggered by every member of the TNF-R family with the exception of Fas and DR4. TNFL1 also leads to apoptosis of activated T cells, a well documented effect in the case of Fas ligand and TNF. TNFL1 differs in its expression pattern, however, when compared to TNF or Fas ligand. Fas ligand, which is involved in activation-induced cell death (AICD) of CD4+ T cells and tolerance to self-antigens, is classically expressed on activated T cells and the immuno-priviliged eye and testis. TNF is constitutively expressed on both mature and immature thymocytes, is upregulated on activated T cells, and is induced by LPS on macrophages. In contrast, TNFL1 is constitutively expressed on antigen presenting cells, specialized or not, such as monocytes, B cells from peripheral blood lymphocytes in humans, and likely on macrophages or dendritic cells in the red pulp and marginal zone of mouse spleen and cultured dendritic cells.

This localization in the blood and in the spleen suggests a possible function for TNFL1 in the recognition process of blood-borne pathogens, such as bacteria or viruses. Furthermore, TNFL1 is expressed at the surface of dendritic cells cultured from bone marrow in the presence of GM-CSF. TNFL1 may therefore be expressed on a subtype of dendritic cells which were recently individualized, myeloid dendritic cells (MDCs), rather than on lymphoid dendritic cells (LDCs). MDCs share a precursor with macrophages, are GM-CSF dependant, and are present in the marginal zone of secondary lymphoid tissues. LDCs, in contrast, are located in the T-cell zone of the secondary organs, are IL3-dependent, and share a precursor with T and B cells.

A second cDNA clone was isolated from an oligodT-primed library of a human ovarian tumor. It encodes a protein designated as TNFL2, which has about 25% homology with TNF. TNFL2 does not have a transmembrane domain and thus can be secreted. The sequence of TNFL2 is shown in SEQ ID NO:5. The TNFL2 cDNA clone detects a major population of mRNA in a range of about 1.5 kb to about 2 kb in tissues associated with the immune system, eg., peripheral blood lymphocytes and spleen. A slightly bigger mRNA is also expressed in spleen as well as in colon, prostate, and to a lesser extent in ovary and small intestine. The fill length polynucleotide sequence of TNFL2 cDNA is shown in SEQ ID NO:10.

TNFL1 might be able to bind to the TNF receptors or to Fas, as a homotrimer or in association with another member of the TNF family. TNFL1 and TNFL2 may form heterodimers and work together in a manner similar to that of lymphotoxin α and β. The TNF-like ligands disclosed herein can be used, inter alia, to induce cell death in tumors, to induce apoptosis of activated T cells, to induce inflammation, and to rescue resting T cells from apoptosis.

Proteins which are members of the TNFR superfamily have also been identified. These are soluble receptors which have the amino acid sequences shown in SEQ ID NOS:2 and 3 (human) and SEQ ID NO:4 (mouse). These proteins are encoded by the nucleotide sequences shown in SEQ ID NOS:7, 8, and 9, respectively. These receptors can be used, inter alia, to regulate the function of a TNF ligand which plays a role in apoptosis, inflammation, differentiation, or proliferation. Expression of the. receptors can also be useful as markers for cancer, especially for colon cancer. Diseases which can be treated using the ligands and/or receptors of the TNF/TNFR superfamily include rheumatoid arthritis, cancer, septic shock, Crohn's disease, and osteoporosis.

Two forms of the soluble receptor corresponding to SEQ ID NO:2 have been identified. The first (tnfrGT-1) has 300 amino acids, as shown in SEQ ID NO:17. The second form (tnfrGT-2) is shown in SEQ ID NO:20. Polynucleotides encoding these two forms are shown SEQ ID NOS:18 and 19, respectively.

The human TNF-like (TNF-L) and mammalian TNF receptor-like (TNFR-L) proteins or polypeptides, biologically active polypeptides or protein variants, and fusion proteins disclosed herein can be used in various therapeutic compositions and methods, as described below. Any naturally occurring variants of SEQ ID NOS:1–5 which may occur in human or mammalian tissues and which retain the functional properties of the TNF-L or TNFR-L proteins disclosed herein are biologically active TNF-L or TNFR-L variants. Non-naturally occurring TNF-L or TNFR-L variants which contain conservative amino acid substitutions relative to SEQ ID NOS:1–5 but which retain substantially the same ligand or receptor activity as naturally occurring TNF-L or TNFR-L are also biologically active TNF-L or TNFR-L variants.

Naturally or non-naturally occurring TNF-L or TNFR-L variants preferably are at least 85%, 90%, or 95% identical to SEQ ID NOS:1–5 and have similar biological functions, which are described below. More preferably, the molecules are 98% or 99% identical. Percent identity is determined using the Smith-Waterman homology search algorithm, using an affine gap search with a gap open penalty of 12 and a gap extension penalty of 1. The Smith-Waterman homology search algorithm is taught in Smith and Waterman, *Adv. AppL. Math.* (1981) 2:482–489.

Biologically active TNF-L or TNFR-L variants include glycosylated forms of the proteins, aggregative conjugates of the proteins with other molecules, and covalent conjugates of the proteins with unrelated chemical moieties. Covalent conjugates are prepared by linkage of functionalities to groups which are found in the amino acid chain or at the N- or C-terminal residues of the proteins of the invention by means well known in the art. TNF-L or TNFR-L variants also include allelic variants, species variants, and muteins. Truncations or deletions of regions which do not affect the biological functions of the TNF-L or TNFR-L proteins disclosed herein are also biologically active TNF-L or TNFR-L variants.

A subset of mutants, called muteins, is a group of polypeptides with the non-disulfide bond participating cysteines substituted with a neutral amino acid, generally, with serines. These mutants may be stable over a broader temperature range than naturally occurring TNF-L or TNFR-L proteins. See Mark et al., U.S. Pat. No. 4,959,314.

Biologically active TNF-L or TNFR-L polypeptides can comprise at least 6, 7, 8, 9, 10, 12, 15, 20, 25, 30, 35, 40, 50, 75, 100, 125, 150, 175, 200, 225, 250, or 275 contiguous amino acids of SEQ ID NO:1, at least 6, 7, 8, 9, 10, 12, 15, 20, 25, 30, 35, 40, 50, 75, 100, 125, or 150 contiguous amino acids of SEQ ID NO:2, at least 6, 7, 8, 9, 10, 12, 15, 20, 25, 30, 35, 40, 50, 75, 100, 125, 150, 175, or 200 contiguous amino acids of SEQ ID NO:3, at least 6, 7, 8, 9, 10, 12, 15, 20, 25, 30, 35, 40, 50, 75, 100, 125, 130, or 140 contiguous amino acids of SEQ ID NO:4, or at least 6, 7, 8, 9, 10, 12, 15, 20, 25, 30, 35, 40, 50, 75, 100, 125, 150, 175, or 200 contiguous amino acids of SEQ ID NO:5, at least 6, 7, 8, 9, 10, 12, 15, 20, 25, 30, 35, 40, 45, 50, 75, 100, 125, 150, 175, 200, 225, 230, 231, 240, 250, 275, or 295 contiguous amino acids of SEQ ID NO:17, or at least 6, 7, 8, 9, 10, 12, 15, 20, 25, 30, 35, 40, 45, 50, 75, 100, 125, 150, 175, 200, or 210 contiguous amino acids of SED ID NO:20. Polypeptide molecules having substantially the same amino acid sequences as the TNF-L or TNFR-L proteins disclosed herein but possessing minor amino acid substitutions which do not substantially affect the ability of the TNF-L or TNFR-L polypeptides to interact with their respective receptors or ligands are within the definition of biologically active TNF-L or TNFR-L polypeptide variants.

Preferably, biologically active TNF-L or TNFR-L polypeptides or polypeptide variants are at least 65%, 75%, 85%, 90%, 95%, 98%, or 99% identical to TNF-L or TNFR-L polypeptide fragments of SEQ ID NOS:1–5, 17 or 20. Percent identity of potential polypeptides or polypeptide variants with fragments of SEQ ID NOS:1–5, 17 or 20 is determined as described above.

Guidance in determining which amino acid residues can be substituted, inserted, or deleted without abolishing biological or immunological activity can be found using computer programs well known in the art, such as DNASTAR software. Preferably the amino acid changes in TNF-L or TNFR-L protein or polypeptide variants are conservative amino acid changes, i.e., changes of similarly charged or uncharged amino acids. Conservative replacements are those which take place within a family of amino acids which are related in their side chains. Genetically encoded amino acids are generally divided into four families: acidic (aspartate, glutamate); basic (lysine, arginine, histidine); non-polar (alanine, valine, leucine, isoleucine, proline, phenylalanine, methionine, tryptophan); and uncharged polar (glycine, asparagine, glutamine, cystine, serine, threonine, tyrosine). Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting TNF-L or TNFR-L molecule, especially if the replacement does not involve an amino acid at a binding site involved in an interaction of a TNF-L protein with its receptor or a TNFR-L protein with its ligand. Binding between a TNF-L protein and its receptor or a TNFR-L protein and its ligand can be measured, for example, using a yeast two-hybrid assay, as is known in the art (Fields & Song, Nature 340:245–46, 1989).

Alternatively, the amino acid sequence of a TNF-L or TNFR-L protein can be modified to alter its biological activity. For example, amino acids 174–193 (the TNF ligand binding domain) can be deleted in a TNFR-L protein to form an inactive variant of the TNFR-L protein and thereby inhibit or decrease the function of its ligand.

TNF-L or TNFR-L proteins or polypeptides can be isolated from TNF-L and TNFR-L-producing cells, such as spleen, thymus, prostate, colon, ovary, small intestine, peripheral blood lymphocytes, or from cell lines such as K562 (chronic myeoleukemia), G361 (melanoma), or SW480 (colorectal adenocarcinoma), using biochemical methods which are standard in the art. These methods include, but are not limited to, size exclusion chromatography, ammonium sulfate fractionation, ion exchange chromatography, affinity chromatography, crystallization, electrofocusing, and preparative gel electrophoresis. The skilled artisan can readily select methods which will result in a preparation of TNF-L or TNFR-L protein which is substantially free from other proteins and from carbohydrates, lipids, or subcellular organelles. A preparation of isolated and purified TNF-L or TNFR-L protein is at least 80% pure; preferably, the preparations are 90%, 95%, or 99% pure. Purity of the preparations can be assessed by any means known in the art, such as SDS-polyacrylamide gel electrophoresis.

Human TNF-L and human or mammalian TNFR-L proteins, polypeptides, or variants can be produced by recombinant DNA methods or by synthetic chemical methods. For production of recombinant TNF-L or TNFR-L proteins or polypeptides, coding sequences selected from the nucleotide sequences shown in SEQ ID NOS:6–10, 18 and 19 can be expressed in known prokaryotic or eukaryotic expression systems. Bacterial, yeast, insect, or mammalian expression systems can be used, as is known in the art.

Alternatively, synthetic chemical methods, such as solid phase peptide synthesis, can be used to synthesize human TNF-L or human or mammalian TNFR-L protein, polypeptides, or variants. General means for the production of peptides, analogs or derivatives are outlined in CHEMISTRY AND BIOCHEMISTRY OF AMINO ACIDS, PEPTIDES, AND PROTEINS —A SURVEY OF RECENT DEVELOPMENTS, B. Weinstein, ed. (1983). Substitution of D-amino acids for the normal L-stereoisomer of a TNF-L or TNFR-L protein of the invention can be carried out to increase the half-life of the molecule.

Fusion proteins comprising at least 6, 7, 8, 9, 10, 12, 15, 20, 25, 30, 35, 40, 50, 75, 100, 125, 150, 175, 200, 225, 250, or 275 contiguous amino acids of SEQ ID NO:1, at least 6, 7, 8, 9, 10, 12, 15, 20, 25, 30, 35, 40, 50, 75, 100, 125, or 150 contiguous amino acids of SEQ ID NO:2, at least 6, 7, 8, 9, 10, 12, 15, 20, 25, 30, 35, 40, 50, 75, 100, 125, 150, 175, or 200 contiguous amino acids of SEQ ID NO:3, at least 6, 7, 8, 9, 10, 12, 15, 20, 25, 30, 35, 40, 50, 75, 100, 125, 130, or 140 contiguous amino acids of SEQ ID NO:4, at least 6, 7, 8, 9, 10, 12, 15, 20, 25, 30, 35, 40, 50, 75, 100, 125, 150, 175, or 200 contiguous amino acids of SEQ ID NO:5, at least 6, 7, 8, 9, 10, 12, 15, 20, 25, 30, 35, 40, 45, 50, 75, 100, 125, 150, 175, 200, 225, 230, 231, 240, 250, 275, or 295 contiguous amino acids of SEQ ID NO:17, or at least 6, 7, 8, 9, 10, 12, 15, 20, 25, 30, 35, 40, 45, 50, 75, 100, 125, 150, 175, 200, or 210 contiguous amino acids of SEQ ID NO:20 can also be constructed. TNF-L and TNFR-L fusion proteins are useful for generating antibodies against TNF-L and TNFR-L amino acid sequences and for use in various assay systems. For example, TNF-L and TNFR-L fusion proteins can be used to identify proteins which interact with these proteins which influence their biological activity and/or ability to bind to their respective binding partners. Physical methods, such as protein affinity chromatography, or library-based assays for protein-protein interactions such as the yeast two-hybrid or phage display systems, can also be used for this purpose. Such methods are well known in the art and can also be used as drug screens.

A TNF-L or TNFR-L fusion protein comprises two protein segments fused together by means of a peptide bond.

The first protein segment consists of at least 6, 7, 8, 9, 10, 12, 15, 20, 25, 30, 35, 40, 50, 75, 100, 125, 150, 175, 200, 225, 250, or 275 contiguous amino acids of SEQ ID NO:1, at least 6, 7, 8, 9, 10, 12, 15, 20, 25, 30, 35, 40, 50, 75, 100, 125, or 150 contiguous amino acids of SEQ ID NO:2, at least 6, 7, 8, 9, 10, 12, 15, 20, 25, 30, 35, 40, 50, 75, 100, 125, 150, 175, or 200 contiguous amino acids of SEQ ID NO:3, at least 6, 7, 8, 9, 10, 12, 15, 20, 25, 30, 35, 40, 50, 75, 100, 125, 130, or 140 contiguous amino acids of SEQ ID NO:4, at least 6, 7, 8, 9, 10, 12, 15, 20, 25, 30, 35, 40, 50, 75, 100, 125, 150, 175, or 200 contiguous amino acids of SEQ ID NO:5, at least 6, 7, 8, 9, 10, 12, 15, 20, 25, 30, 35, 40, 45, 50, 75, 100, 125, 150, 175, 200, 225, 230, 231, 240, 250, 275, or 295 contiguous amino acids of SEQ ID NO:17, or at least 6, 7, 8, 9, 10, 12, 15, 20, 25, 30, 35, 40, 45, 50, 75, 100, 125, 150, 175, 200, or 210 contiguous amino acids of SEQ ID NO:20. The amino acids can be selected from the amino acid sequences shown in SEQ ID NOS:1–5, 17 or 20 or from a biologically active variants of those sequences. The first protein segment can also be a full-length TNF-L or TNFR-L protein comprising an amino acid sequence as shown in SEQ ID NOS:1–5, 17 or 20. The first protein segment can be N-terminal or C-terminal, as is convenient.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (UMP), S-tag, Lex A DNA binding domain (DBD) fusions, GAL4 DNA binding domain fusions, and herpes simplex virus (HSV) BP16 protein fusions.

According to one particularly preferred embodiment, a TNFR-L protein is fused to the Fc domain of an IgG1 molecule. Such a fusion protein is be useful for inhibiting the action of a TNF ligand.

TNF-L or TNFR-L fusion proteins can be made by covalently lining the first and second protein segments or by standard procedures in the art of molecular biology. Recombinant DNA methods can be used to prepare the fusion proteins, for example, by making a DNA construct which comprises coding sequences selected from SEQ ID NOS:6–10, 18, and 19 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated TNF-L or TNFR-L proteins, polypeptides, biologically active variants, or fusion proteins can be used as immunogens, to obtain a preparation of antibodies which specifically bind to epitopes of INF-L or TNFR-L proteins. The antibodies can be used, inter alia, to detect TNF-L or TNFR-L proteins in tissue of humans or other mammals or in fractions thereof The antibodies can also be used to detect the presence of mutations in genes which result in under- or over-expression of TNF-L or TNFR-L proteins or in expression of a TNF-L or TNFR-L protein with altered size or electrophoretic mobility. By binding to TNF-L or TNFR-L proteins, antibodies can also alter the binding properties or biological functions of the proteins, for example for therapeutic use.

Antibodies which specifically bind to epitopes of TNF-L or TNFR-L proteins, polypeptides, fusion proteins, or biologically active variants can be used in immunochemical assays, including but not limited to Western blots, ELISAs, radioimmunoassays, immunohistochemical assays, inmunoprecipitations, or other immunochemical assays known in the art. Typically, antibodies provide a detection signal at least 5-, 10-, or 20-fold higher than a detection signal provided with other proteins when used in such immunochemical assays. Preferably, antibodies which specifically bind to TNF-L or TNFR-L protein epitopes do not detect other proteins in immunochemical assays and can immunoprecipitate TNF-L or TNFR-L proteins or polypeptides from solution.

TNF-L- or TNFR-L-specific antibodies specifically bind to epitopes present in a protein having the amino acid sequence shown in SEQ ID NOS:1–5, 17 and 20 or to biologically active variants of those sequences. Typically, at least 6, 8, 10, or 12 contiguous amino acids are required to form an epitope. However, epitopes which involve non-contiguous amino acids may require more, e.g., at least 15, 25, or 50 amino acids. Preferably, TNF-L or TNFR-L epitopes are not present in other proteins. A preferred epitope comprises amino acids 208–211 of SEQ ID NO:20. Antibodies capable of specifically binding to a protein comprising this epitope are useful for identifying a protein expressed by the polynucleotide of SEQ ID NO:19.

Protein epitopes which are particularly antigenic can be selected, for example, by routine screening of polypeptides for antigenicity or by applying a theoretical method for selecting antigenic regions of a protein to the amino acid sequences shown in SEQ ID NOS:1–5. Such methods are taught, for example, in Hopp and Wood, *Proc. Natl. Acad Sci. U.S.A.* 78, 3824–28 (1981), Hopp and Wood, *Mol. Immunol.* 20, 483–89 (1983), and Sutcliffe el al., *Science* 219, 660–66 (1983).

Any type of antibody known in the art can be generated to bind specifically to TNF-L or TNFR-L epitopes. For example, preparations of polyclonal and monoclonal antibodies can be made using standard methods which are well known in the art. Similarly, single-chain antibodies can also be prepared. Single-chain antibodies which specifically bind to TNF-L or TNFR-L epitopes can be isolated, for example, from a single-chain immunoglobulin display library, as is known in the art. The library is "panned" against the amino acid sequences disclosed herein, and a number of single chain antibodies which bind with high-affinity to different epitopes of proteins of the invention can be isolated. Hayashi el al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159–63. Construction of bivalent, bispecific single-chain antibodies is taught inter alia in Mallender and Voss, 1994, *J Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to TNF-L or TNFR-L epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies can be purified by methods well known in the art. For example, antibodies can be affinity purified by passing the antibodies over a column to which a TNF-L or TNFR-L protein, polypeptide, biologically active variant, or fusion protein is bound. The bound antibodies can then be eluted from the column, using a buffer with a high salt concentration.

TNF-L- or TNFR-L-specific binding polypeptides other than antibodies can also be identified. These polypeptides include ligands of TNFR-L proteins and receptors of TNF-L proteins. TNF-L- or TNFR-L-specific binding polypeptides are polypeptides which bind with TNF-L or TNFR-L proteins or their variants and which have a measurably higher binding affinity for TNF-L or TNFR-L and polypeptide variants of these proteins than for other polypeptides tested for binding. Higher affinity by a factor of 10 is preferred, more preferably a factor of 100. Such polypeptides can be found, for example, using the yeast two-hybrid system.

Nucleotide sequences which encode TNF-L or TNFR-L proteins are shown in SEQ ID NOS:6–10, 18 and 19. Isolated and purified polynucleotides according to the invention can be single- or double-stranded, are subgenomic, and contain less than a whole chromosome. Preferably, the subgenomic polynucleotides are intron-free.

Isolated and purified subgenomic polynucleotides according to the invention can comprise at least 10, 11, 12, 13, 14, 15, 16, 17, 18, 19, 20, 21, 22, 23, 24, 25, 30, 35, 40, 45, 50, 75, 100, 150, 200, 250, 300, 350, 400, 450, 500, 600, 700, 800, 900, 1000, 1100, or 1200 contiguous nucleotides of SEQ ID NO:6, at least 10, 11, 12, 13, 14, 15, 16, 17, 18, 19, 20, 21, 22, 23, 24, 25, 30, 35, 40, 45, 50, 75, 100, 150, 200, 250, 300, 350, 400, or 450 contiguous nucleotides of SEQ ID NO:7, at least 10, 11, 12, 13, 14, 15, 16, 17, 18, 19, 20, 21, 22, 23, 24, 25, 30, 35, 40, 45, 50, 75, 100, 150, 200, 250, 300, 350, 400, 450, 500, 550, 575, 600, 650, 700, 750, 800, or 850 contiguous nucleotides of SEQ ID NO:8, at least 10, 11, 12, 13, 14, 15, 16, 17, 18, 19, 20, 21, 22, 23, 24, 25, 30, 35, 40, 45, 50, 75, 100, 150, 200, 250, 300, 350, 400, 450, 500, 550, 575, or 600 contiguous nucleotides of SEQ ID NO:9, or at least 10, 11, 12, 13, 14, 15, 16, 17, 18, 19, 20, 21, 22, 23, 24, 25, 30, 35, 40, 45, 50, 75, 100, 150, 200, 250, 300, 350, 400, 450, 500, 600, 700, 800, 900, 1000, 1100, or 1200 contiguous nucleotides of SEQ ID NO:10, at least 10, 11, 12, 13, 14, 15, 16, 17, 18, 19, 20, 21, 22, 23, 24, 25, 30, 35, 40, 45, 50, 75, 100, 150, 200, 250, 300, 350, 400, 450, 500, 600, 700, 800, 900, 1000, 1100, 1200, 1250, 1300, 1400, 1500, 1600, 1700, 1800, or 1830 contiguous nucleotides of SEQ ID NO:19, or can comprise SEQ ID NOS:6, 7, 8, 9, 10, 18, or 19. Such polynucleotides can be used, for example, as primers or probes or for expression of TNF-L or TNFR-L proteins or polypeptides.

The complements of the nucleotide sequences shown in SEQ ID NOS:6–10, 18, and 19 are contiguous nucleotide sequences which form Watson-Crick base pairs with a contiguous nucleotide sequence as shown in SEQ ID NOS:6–10, 18, and 19. The complements of SEQ ID NOS:6–10, 18, and 19 are polynucleotides of the invention and can be used, for example, to provide antisense oligonucleotides, primers, and probes.

Antisense oligonucleotides, primers, and probes of the invention can consist of at least 11, 12, 15, 20, 25, 30, 50, or 100 contiguous nucleotides which are complementary to the coding sequences shown in SEQ ID NOS:6–10, 18, and 19. A complement of the entire coding sequence can also be used. Double-stranded subgenomic polynucleotides which comprise all or a portion of the nucleotide sequences shown in SEQ ID NOS:6–10, 18, and 19, as well as polynucleotides which encode TNF-L- or TNFR-L-specific antibodies or ribozymes, are also subgenomic polynucleotides according to the invention.

Degenerate nucleotide sequences encoding amino acid sequences of proteins or biologically active protein variants as well as homologous nucleotide sequences which are at least 65%, 75%, 85%, 90%, 95%, 96%, 97%, 98%, or 99% identical to the nucleotide sequences shown in SEQ ID NOS:6–10, 18, or 19 are also subgenomic polynucleotides according to the invention and can be used in the methods disclosed herein. Percent sequence identity between a nucleotide sequence of SEQ ID NOS:6–10, 18 or 19 and a putative homologous or degenerate nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequences shown in SEQ ID NOS:6–10, 18 or 19, or their complements with at most 1, 2, 3, 4, 5, 10, 15, 20, 25, 30, or 35% basepair mismatches are also TNF-L or TNFR-L subgenomic polynucleotides. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous TNF-L or TNFR-L sequences can be identified which contain at most about 25–30% basepair mismatches with SEQ ID NOS:6–10, 18 or 19, or their complements. More preferably, homologous nucleic acid strands contain 15–25% basepair mismatches, even more preferably 5–15% basepair mismatches.

Species homologs of TNF-L or TNFR-L subgenomic polynucleotides of the invention can also be identified by making suitable probes or primers and screening cDNA expression libraries from other species, such as mice, monkeys, yeast, or bacteria. It is well known that the $T_m$ of a double-stranded DNA decreases by 1–1.5° C. with every 1% decrease in homology (Bonner et al., *J. Mol. Biol.* 81, 123 (1973). Homologous TNF-L or TNFR-L human polynucleotides or TNF-L or TNFR-L polynucleotides of other species can therefore be identified, for example, by hybridizing a putative homologous TNF-L or TNFR-L polynucleotide with a polynucleotide having a nucleotide sequence of SEQ ID NO:6, 7, 8, 9, 10, 18, or 19, comparing the melting temperature of the test hybrid with the melting temperature of a hybrid comprising a polynucleotide having a nucleotide sequence of SEQ ID NOS:6, 7, 8, 9, 10, 18, or 19 and a polynucleotide which is perfectly complementary to SEQ ID NO:6, 7, 8, 9, 10, 18, or 19, and calculating the number of basepair mismatches within the test hybrid.

Nucleotide sequences which hybridize to the coding sequences shown in SEQ ID NOS:6–10, 18, or 19, or their complements following stringent hybridization and/or wash conditions are also TNF-L or TNFR-L subgenomic polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a sequence shown in SEQ ID NO:6, 7, 8, 9, 10, 18 or 19, and a polynucleotide sequence which is 65%, 75%, 85%, 90%, 95%, 96%, 97%, 98%, or 99% identical to SEQ ID NO:6, 7, 8, 9, 10, 18, or 19 can be calculated, for example, using the equation of Bolton and McCarthy, *Proc. Natl. Acad. Sc. U.S.A.* 48, 1390 (1962):

$$T_m=81.5° C.-16.6(\log_{10}[Na^+])+0.41(\%G+C)-0.63(\%\text{formamide})-600/l),$$

where $l$=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Subgenomic polynucleotides can be isolated and purified free from other nucleotide sequences using standard nucleic acid purification techniques. For example, restriction enzymes and probes can be used to isolate subgenomic polynucleotide fragments which comprise TNF-L or TNFR-L coding sequences. Isolated and purified subgenomic polynucleotides are in preparations which are free or at least 90% free of other molecules.

Complementary DNA (cDNA) molecules which encode TNF-L or TNFR-L proteins are also TNF-L or YNFR-L subgenomic polynucleotides. cDNA molecules can be made with standard molecular biology techniques, using TNF-L or TNFR-L mRNA as a template. cDNA molecules can thereafter be replicated using molecular biology techniques known in the art and disclosed in manuals such as Sambrook et al., 1989. An amplification technique, such as the polymerase chain reaction IPCR), can be used to obtain additional copies of subgenomic polynucleotides, using either human or mammalian genomic DNA or cDNA as a template.

Alternatively, synthetic chemistry techniques can be used to synthesize subgenoric polynucleotide molecules. The degeneracy of the genetic code allows alternate nucleotide sequences to be synthesized which will encode a TNF-L protein comprising an amino acid sequence shown in SEQ ID NOS:1, 2, 3, 4, 5, 17, 20 or a biologically active variant of one of those sequences.

The invention also provides polynucleotide probes which can be used to detect TNF-L or TNFR-L sequences, for example, in hybridization protocols such as Northern or Southern blotting or in 7 situ hybridizations. TNF-L or TNFR-L polynucleotide probes of the invention comprise at least 12, 13, 14, 15, 16, 17, 18, 19, 20, 30, or 40 or more contiguous nucleotides selected from SEQ ID NOS:6–10, 18, or 19. Polynucleotide probes can comprise a detectable label, such as a radioisotopic, fluorescent, enzynmatic, or chemiluminescent label.

TNF-L or TNFR-L subgenomic polynucleotides can be propagated in vectors and cell lines using techniques well known in the art. Expression systems in bacteria include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, dedoer et al., *Proc. Natl. Acad Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202 :302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5:

3376, U.S. Pat. Nos. 4,837,148, 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. USA* (1984) 81: 1470–1474, Kelly and Hynes, *EMBO J.* (1985) 4: 475479; EP 244,234, and WO 91/00357.

Expression of TNF-L or TNFR-L subgenomic polynucleotides in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al, *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp. 277–279, and Maeda et al., *Nature,* (1985) 315: 592–594.

Mammalian expression of TNF-L or TMNR-L subgenomic polynucleotides can be accomplished as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, 4,560,655, WO 90/103430, WO 87/00195, and U.S. Pat. No. RE 30,985.

TNF-L or TNFR-L subgenornic polynucleotides can be on linear or circular molecules. They can be on autonomously replicating molecules or on molecules without replication sequences. They can be regulated by their own or by other regulatory sequences, as is known in the art. TNF-L or TNFR-L subgenomic polynucleotides can be introduced into suitable host cells using a variety of techniques which are available in the art, such as transferrin-polycation-mediated DNA transfer, transfection with naked or encapsulated nucleic acids, liposome-mediated DNA transfer, intracellular transportation of DNA-coated latex beads, protoplast fusion, viral infection, electroporatiorn and calcium phosphate-mediated transfection.

Polynucleotides of the invention can also be used in gene delivery vehicles, for the purpose of delivering an mItNA or oligonucleotide (either with the sequence of a native mRNA or its complement), full-length protein, fusion protein, polypeptide, or riboyme, or single-chain antibody, into a cell, preferably a eukaryotic cell. According to the present invention, a gene delivery vehicle can be, for example, naked plasmid DNA, a viral expression vector comprising a polynucleotide of the invention, or a polynucleotide of the invention in conjunction with a liposome or a condensing agent.

In one embodiment of the invention, the gene delivery vehicle comprises a promoter and one of the polynucleotides disclosed herein. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91102805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch el al.,*J. Vir.* 49:828, 1984; and Oliff et al.,*J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al.,*J. Vir.* 67:4722, 1993; and Yantchev *Neopksma* 26:397, 1979), Gross (ATCC No. VR-590), Kirsten (Albino et al., *J. Exp. Med.* 164:1710, 1986), Harvey sarcoma virus (Manly el al., *J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al.,*J. Fxp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral gene delivery vehicles given the disclosure provided herein and standard recombinant techniques (e.g., Sambrook et al., 1989, and Kunkle, *Proc. Natl. Acad. Sci. U.S.A.* 82:488, 1985) known in the art. Portions of retroviral expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 071800, 921, filed Nov. 29, 1991). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282).

A gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral gene delivery vehicles can also be constructed and used to deliver proteins or polynucleotides of the invention to cells in vitro or in vivo. The use of adeno-associated viral gene delivery vehicles in vitro is described in Chatteijee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Nat'l Acad. Sci.* 90: 10613–10617(1993), and Kaplitt et al., *Nature Genet.* 8:148–153 (1994).

In another embodiment of the invention, a gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for polynucleotides of the invention. Alpha viruses are described in WO 94/21792, WO 92/10578 and WO 95/07994. Several different alphavirus gene delivery vehicle systems can be constructed and used to deliver polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent fragment transcription, and a Sindbis RNA polymerase recognition sequence. Optionally, the viral junction region can be modified so that polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the polynucleotide and a second viral junction region which has been modified such that polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *PROC. NATL. ACAD. SCI. U.S.A.* 86:317, 1989; Flexner et al., *Ann. N.Y. Acad. Sci.* 569:86, 1989; Flexner et al., *Vaccine* 8:17, 1990; U.S. Pat. Nos. 4,603,112 and 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277: 108, 1979); human immunodeficiency virus (EPO 386,882, Buchschacher et al., *J. Vir.* 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

A polynucleotide of the invention can also be combined with a condensing agent to form a gene delivery vehicle. In a preferred embodiment, the condensing agent is a polycation, such as polylysine, polyarginine, polyornithine, protamine, spermine, spernidine, and putrescine. Many suitable methods for making such linkages are known in the art (see, for example, Ser. No. 08/366,787, filed Dec. 30, 1994).

In an alternative embodiment, a polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry*, pp. 236–240, 1975 (W. H. Freeman, San Francisco, Calif.); Szoka et al., *Biochim.*

*Biophys. Acta* 600:1, 1980; Bayer et al., *Biochim. Biophys. Acta.* 550:464, 1979; Rivnay et al., *Meth. Enzymol.* 149:119, 1987; Wang et al., *PROC. NATL. ACAD. SCI. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413–7416, 1987), mRNA (Malone et al., *Proc. Natl. Acad. Sci. USA* 86:6077–6081, 1989), and purified transcription factors (Debs et al, *J. Biol. Chem.* 265:10189–10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Feigner et al., *Proc. Natl. Acad. Sci. US4* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad Sci. USA* 76:3348, 1979; Enoch and Strittmatter, *Proc. Natl. Acad Sci. USA* 76:145, 1979; Fraley et al., *J. Biol. Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with a polynucleotide of the invention for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked polynucleotide molecules are used as gene delivery vehicles, as described in WO 90/11092 and U.S. Pat. No. 5,580,859. Such gene delivery vehicles can be either DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Feigner et al., *Proc. Natl. Acad. Sci. USA* 84:7413 7417, 1989), liposomes (Wang et al., *Proc. Natl. Acad Sci.* 84:7851–7855, 1987) and microprojectiles (Williams et al., *Proc. Natl. Acad. Sci.* 88:2726–2730, 1991).

One can increase the efficiency of naked polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. Polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of polynucleotides into the cytoplasm.

The newly identified receptor proteins play regulatory roles in cell proliferation and/or differentiation. For example, they can induce the production of cytokines, immunoglobulins, and cell surface antigens. The receptors can also play a role in the negative regulation of osteoclastogenesis. Soluble TNFR-like receptors can be usefull in the neutralization of TNF or TNF-like ligands for the treatment of rheumatoid arthritis and Crohn's disease. Similarly, restoring normal apoptosis to a cell via these receptors can be used to treat viral diseases.

A variety of diseases and conditions can be treated by modulating the activity of TNF-L or TNFR-L proteins of the invention. For example, TNFL proteins induce apoptosis of activated T cells, but rescue resting T cells from apoptosis. A TNF-L protein can therefore be used to treat autoimmune diseases, such as myasthenia gravis, insulin-dependent diabetes mellitus, rheumatoid arthritis, multiple sclerosis, and systemic lupus erythematosus. TNF-L proteins also have tumor stimulating properties. Tumors can therefore be treated by inhibiting expression or activity of a TNF-L protein. Similarly, reducing expression of a TNFR-L protein or blocking its ligand binding site can be used to treat tumors, whereas increasing expression of a TNFR-L protein can be used to treat autoimmune diseases such as those disclosed above.

In one embodiment of the invention, expression of a TVF-L or TNFR-L gene is decreased using a ribozyme, an RNA molecule with catalytic activity. See, e.g., Cech, 1987, *Science* 236: 1532–1539; Cech, 1990, *Ann. Rev. Biochem.* 59:543–568; Cech, 1992, *Curr. Opin. Struct. Biol.* 2: 605–609; Couture and Stinchcomb, 1996, *Trends Genet.* 12: 510–515. Ribozymes can be used to inhibit gene function by cleaving an RNA sequence, as is known in the art (e.g., Haseloff et al., U.S. Pat. No. 5,641,673).

The coding sequences shown in SEQ ID NOS:6–10, 18, and 19 can be used to generate ribozymes which will specifically bind to mRNA transcribed from a TNF-L or TNFR-L gene. Methods of designing and constructing ribozymes which can cleave other RNA molecules in trans in a highly sequence specific manner have been developed and described in the art (see Haseloff et al. (1988), *Nature* 334:585–591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

TNF-L and TNFR-L-specific ribozymes can be introduced into cells, such as neoplastic cells, as part of a DNA construct, as is known in the art. The DNA construct can also include transcriptional regulatory elements, such as a promoter element, an enhancer or UAS element, and a transcriptional terminator signal, for controlling transcription of the ribozyme in the cells.

Mechanical methods, such as microinjection, liposome-mediated transfection, electroporation, or calcium phosphate precipitation, can be used to introduce the ribozyme-containing DNA construct into cells whose division it is desired to decrease, as described above. Alternatively, if it is desired that the cells stably retain the DNA construct, the DNA construct can be supplied on a plasmid and maintained as a separate element or integrated into the genome of the cells, as is known in the art.

Expression of a TNF-L or TNFR-L gene can also be altered using an antisense oligonucleotide sequence. The antisense sequence is complementary to at least a portion of the coding sequence of a gene having a coding sequence shown in SEQ ID NO:6–10, 18, or 19. Preferably, the antisense oligonucleotide sequence is at least six nucleotides in length, but can be about 8, 12, 15, 20, 25, 30, 35, 40, 45, or 50 nucleotides long. Longer sequences can also be used. TNF-L or TNFR-L antisense oligonucleotide molecules can be provided in a DNA construct and introduced into cells whose division is to be decreased, as described above.

Antisense oligonucleotides can be composed of deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1–8; Sonveaux, 1994, *Meth. Mol. Biol.* 26:1–72; Uhlmann et al., 1990, *Chem. Rev.* 90:543–583.

Precise complementarity is not required for successful duplex formation between an antisense molecule and the complementary coding sequence of a TNF-L or TNFR-L gene. Antisense molecules which comprise, for example, 2, 3, 4, or 5 or more stretches of contiguous nucleotides which are precisely complementary to a TNF-L or TNFR-L coding sequence, each separated by a stretch of contiguous nucleotides which are not complementary to adjacent TNF-L or TNFR-L coding sequences, can provide targeting specificity for TNF-L or TNFR-L mRNA. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular TNF-L or TNFR-L coding sequence.

TNF-L or TNFR-L antisense oligonucleotides can be modified without affecting their ability to hybridize to a TNF-L or TNFR-L coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. Agrawal et al., 1992, *Trends Biotechnol.* 10:152–158; Uhlmann et al., 1990, *Chem. Rev.* 90:543–584; Uhlmann et al., 1987, *Tetrahedron. Lett.* 215:3539–3542.

Antibodies which specifically bind to a TNF-L and TNFR-L protein can also be used to alter effective levels of TNF-L or TNFR-L gene expression. TNF-L and TNFR-L-specific antibodies bind to TNF-L and TNFR-L proteins and prevent the proteins from functioning in the cell. Construction of such antibodies is disclosed above.

Expression of an endogenous TNF-L or TNFR-L gene in a cell can also be altered by introducing in frame with the endogenous TNF-L or TNFR-L gene a DNA construct comprising a TNF-L or TNFR-L targeting sequence, a regulatory sequence, an exon, and an unpaired splice donor site by homologous recombination, such that a homologously recombinant cell comprising the DNA construct is formed. The new transcription unit can be used to turn the YNF-L or TNFR-L gene on or off as desired. This method of affecting endogenous gene expression is taught in U.S. Pat. No. 5,641,670.

The targeting sequence is a segment of at least 10, 12, 15, 20, or 50 contiguous nucleotides selected from a nucleotide sequence shown in SEQ ID NO:6–10, 18, or 19. The transcription unit is located upstream of a coding sequence of the endogenous TNF-L or TNFR-L gene. The exogenous regulatory sequence directs transcription of the coding sequence of the TNF-L or TNFR-L gene.

Preferably, the mechanism used to decrease expression of the TNF-L or TNFR-L gene, whether ribozyme, antisense nucleotide sequence, or antibody, decreases expression of the gene by 50%, 60%, 70%, or 80%. Most preferably, expression of the gene is decreased by 90%, 95%, $^{99}$%, or 100%. The effectiveness of the mechanism chosen to alter expression of the gene can be assessed using methods well known in the art, such as hybridization of nucleotide probes to mRNA of the gene, quantitative RT-PCR, or detection of a TNF-L and TNFR-L protein using specific antibodies of the invention.

TNF-L and TNFR-L proteins or subgenomic polynucleotides can be used in therapeutic compositions for treating a variety of TNF-mediated disorders. Therapeutic compositions of the invention which comprise TNF-L protein or TNF-L protein encoding polynucleotides can be used, for example, to treat disorders in which abnormal numbers of T cells become activated. Activated T-lymphocytes are associated with disease in graft versus host reactions (e.g., bone marrow transplantation) and most forms of autoimmunity, including but not restricted to, multiple sclerosis, rheumatoid arthritis, lupus, and myasthenia gravis. T-lymphocyte-mediated primary diseases, such as juvenile diabetes, can also be treated using TNF-L protein or protein encoding polynucleotides.

TNF-L and TNFR-L therapeutic compositions of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates.

TNF-L or TNFR-L therapeutic compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a therapeutic TNF-L or TNFR-L composition.

Typically, a therapeutic TNF-L or TNFR-L composition is prepared as an injectable, either as a liquid solution or suspension; however, solid forms suitable for solution in, or suspension in, liquid vehicles prior to injection can also be prepared. A TNF-L or TNFR-L composition can also be formulated into an enteric coated tablet or gel capsule according to known methods in the art, such as those described in U.S. Pat. No. 4,853,230, EP 225,189, AU 9,224,296, and AU 9,230,801.

Proliferative disorders, such as neoplasias, dysplasias, and hyperplasias, can be treated by administration of a therapeutic TNF-L and TNFR-L composition which will inhibit TNF-L activity or expression. Neoplasias which can be treated with the therapeutic composition include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors.

Proliferative disorders which can be treated with a therapeutic TNF-L composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias, or pseudoepitheliomatous hyperplasia of the skin can be treated with TNF-L or TNFR-L therapeutic compositions.

Even in disorders in which TNF-L or TNFR-L mutations are not implicated, decreasing expression of a TNF-L gene or a TNFR-L gene or decreasing a TNF-L or TNFR-L protein function can have a therapeutic application. In these disorders, decreasing TNF-L or TNFR-L expression or function can help to suppress tumors. Similarly, in tumors in which TNF-L or TNFR-L expression is not aberrant, effecting TNF-L or TNFR-L downregulation or decrease of TNF-L or TNFR-L activity can suppress metastases.

Administration of therapeutic compositions of the invention can include local or systemic administration, including injection, oral administration, particle gun, or catheterized administration, and topical administration. Various methods can be used to administer a therapeutic composition directly to a specific site in the body. For example, a small metastatic lesion can be located and a therapeutic composition injected several times in several different locations within the body of tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic composition can be directly administered to the surface of a tumor, for example, by topical application of the composition. X-ray imaging can be used to assist in certain of the above delivery methods. Combination therapeutic agents, such as an anti-TNF-L neutralizing antibody and another therapeutic agent, can be administered simultaneously or sequentially.

Alternatively, a therapeutic composition can be introduced into human cells ex vivo, and the cells then replaced into the human. Cells can be removed from a variety of locations including, for example, from a selected tumor or from an affected organ. In addition, the therapeutic composition can be inserted into non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with the therapeutic composition utilizing any of the above-described techniques, followed by the return of the cells to the human, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

Receptor-mediated targeted delivery of therapeutic compositions containing TNF-L or TNFR-L subgenomic polynucleotides to specific tissues can also be used. Receptor-mediated DNA delivery techniques are described in, for example, Findeis et al. (1993), Trends in Biotechnol. 11, 202–05; Chiou et al. (1994), GENE THERAPEUTICS: METHODS AND APPLICATIONS OF DIRECT GENE TRANSFER (J. A. Wolff, ed.); Wu & Wu (1988), J. Biol. Chem. 263, 621–24; Wu et al. (1994), J. Biol. Chem. 269, 542–46; Zenke et al. (1990), Proc. Natl. Acad. Sci. U.S.A. 87, 3655–59; Wu et al. (1991), J. Biol. Chem. 266, 338–42.

Both the dose of the TNF-L or TNFR-L composition and the means of administration can be determined based on the specific qualities of the therapeutic composition, the condition, age, and weight of the patient, the progression of the disease, and other relevant factors. If the composition contains TNF-L or TNFR-L protein, polypeptide, or antibody, effective dosages of the composition are in the range of about 5 µg to about 50 µg/kg of patient body weight, about 50 µg to about 5 µg/kg, about 100 µg to about 500 µg/kg of patient body weight, and about 200 to about 250 µg/kg.

Therapeutic compositions containing TNF-L or TNFR-L subgenomic polynucleotides, ribozymes, or antisense oligonucleotides can be admninistered in a range of about 100 ng to about 200 mg of DNA for local administration in a gene therapy protocol. Concentration ranges of about 500 ng to about 50 mg, about 1 µg to about 2 µg, about 5 µg to about 500 µg, and about 20 µg to about 100 µg of DNA can also be used during a gene therapy protocol. Factors such as method of action and efficacy of transformation and expression are considerations that will effect the dosage required for ultimate efficacy of the TNF-L or TNFR-L subgenomic polynucleotides.

Where greater expression is desired over a larger area of tissue, larger amounts of a TNF-L or TNFR-L therapeutic composition or the same amount readninistered in a successive protocol of administrations, or several administrations to different adjacent or close tissue portions of for example, a tumor site, may be required to effect a positive therapeutic outcome. In all cases, routine experimentation in clinical trials will determine specific ranges for optimal therapeutic effect.

The invention provides knock-out mammals whose endogenous TNF-L or TNFR-L gene is not expressed. Methods of making knock-out mammals are well known in the art. The mammal can be any experimental mammal, such as a mouse, rat, or rabbit; however, a mouse is preferred. The endogenous wild-type TNF-L or TNFR-L gene of the mammal can be deleted entirely, resulting in an absence of TNF-L or TNFRL protein in the mammal. Alternatively, mutations such as deletions, insertions, missense substitutions, or inversions, can be introduced into a TNF-L or TNFR-L gene. Such mutations result in expression of truncated or otherwise aberrant forms of TNF-L or TNFR-L protein in the knock-out mammal. Mammalian cell lines which do not express an endogenous TNF-L or TNFR-L gene can also be constructed, as is known in the art.

Knock-out mammals and cells of the invention are useful as model systems for studying the effects of drugs in the absence of wild-type TNF-L or TNFR-L protein or in the presence of altered forms of the TNF-L or TNFR-L protein in the mammal or cell. Knock-out mammals can also be used to develop therapeutic treatments for diseases associated with alterations in TNF-L or TNFR-L gene expression, such as neoplasia or various autoimmune diseases.

The invention also provides screening methods which can be used to identify chemical agents which may have use in therapy. for example, regulators of the disclosed genes and proteins can be screened using a variety of methods. These include ligand binding (Zhang et al., *J. Biol. Chem.* 267:24069–24075), cytotoxicity (Creasey, *Cancer Res.* 47:145–149, 1987; Geigert, *Develop. Biol. Standard* 69:129; Tsujimoto, *J. Biochem.* 101:919–925, 1987; Kamijo, *Biochem. Biophys. Res. Commun.* 160:830–825, 1989; Sidhu, *Anticancer Res.* 9:1569–1576, 1989), differentiation (Kamijo, 1989), maturation of osteoclasts from hematopoietic precursors (Lacey, *Endocrinolosy* 136:2367–2376, 1995), and proliferation (Tsujimoto, 1989).

The ability of a test compound or a potential therapeutic agent to stimulate or inhibit activity of a TNF-L or TNFR-L protein can be assessed by determining or measuring the viability of the population of cells. A test compound which increases or decreases cell lysis or cell death is a modulator of the TNF-L or TNF-LR protein and can be used as a therapeutic agent to regulate TNF activities, such as cell lysis or cell death. A test compound which increases cell lysis or cell death may be particularly useful in treatment of neoplastic growth. The polypeptide of the invention can be applied to the cell exogenously, or it can be expressed by a cell which has been transfected with a subgenomic polynucleotide encoding the polypeptide.

Methods for measuring the viability of cells can be any which are known in the art. Cell death can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for this purpose is trypan blue. Viability of cells can also be determined by detecting DNA synthesis. Cells can be cultured in cell medium with labeled nucleotides, such as [$^3$H]-thymidine. The uptake or incorporation of the labeled nucleotides by cells indicates DNA synthesis and cell viability. Death of tumor cells in vivo can be monitored by observing regression or shrinkage of a tumor. Any suitable diagnostic technique can be applied.

Other cellular proteins which are involved in the same biological pathways can be identified by looking for proteins which interact with the disclosed polypeptides. Natural ligands can therefore be identified for the receptor proteins, and natural receptor proteins can be identified for the ligands. Complex formation can be detected in vitro or in vivo. Many methods for detecting formation of protein complexes are known in the art, and any such methods can be used. For example, the yeast two-hybrid system can be used in cells to detect proteins which interact with the disclosed ligands and receptors. Alternatively, protein complex formation can be tested in vitro and complexes detected by altered mobility on non-denaturing gels, or by co-immunoprecipitation.

Expression of TNFR-L proteins can serve as a marker of neoplasia. TNFR-L proteins can be detected in body samples, including tissues, serum, urine, sputum, and feces, using immunological techniques. Expression can also be observed by measuring or detecting mRNA encoding the receptors. Any suitable technique can be used including but not limited to Northern blotting and RT-PCR.

A TNF-L or TNFR-L subgenomic polynucleotide can also be delivered to subjects for the purpose of screening test compounds for those which are useful for enhancing transfer of TNF-L or TNFR-L subgenomic polynucleotides to the cel or for enhancing subsequent biological effects of TNF-L or TNFR-L subgenornic polynucleotides within the cell. Such biological effects include hybridization to complementary TNF-L or TNFR-L mRNA and inhibition of its translation, expression of a TNF-L or TNFR-L subgenomic polynucleotide to form a TNF-L or TNFR-L mRNA, single-chain antibody, riboyme, oligonucleotide, or protein and/or replication and integration of a TNF-L or TNFR-L subgenomic polynucleotide. The subject can be a cell culture or an animal, preferably a mammal, more preferably a human.

Test compounds which can be screened include any substances, whether natural products or synthetic, which can be administered to the subject in vitro or in vivo. Libraries or mixtures of test compounds can be tested. The test compound can be a pharmacologic agent already known in the art or can be a compound previously unknown to have any pharmacological activity. The test compound can be naturally occurring or designed in the laboratory. It can be isolated from microorganisms. animals, or plants, and can be produced recombinantly, or synthesized by chemical methods known in the art. Test compounds or substances can be delivered before, after, or concomitantly with a TNF-L or TNFR-L subgenomic polynucleotide. They can be administered separately or in admixture with a TNF-L or TNFR-L subgenomic polynucleotide.

Integration of a delivered TNF-L or TNFR-L subgenomic polynucleotide can be monitored by any means known in the art. For example, Southern blotting of the delivered TNF-L or TNFR-L subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to a TNF-L or TNFR-L probe. Expression of a TNF-L or TNFR-L subgenomic polynucleotide can be monitored by detecting production of TNF-L or TNFR-L mRNA which hybridizes to the delivered polynucleotide or by detecting TNF-L or TNFR-L protein. TNF-L or TNFR-L protein can be detected immunologically. Thus, the delivery of TNF-L or TNFR-L subgenomic polynucleotides according to the present invention provides an excellent system for screening test compounds for their ability to enhance transfer of TNF-L or TNFR-L polynucleotides to a cell, by enhancing delivery, integration, hybridization, expression, replication or integration in a cell in vitro or in vivo in an animal, preferably a mammal, more preferably a human.

The TNFL1 gene (SEQ ID NO:6) maps to human chromosome 13q34. Polynucleotide probes of TNFL1 can therefore be used to identify this region of chromosome 13 in metaphase spreads of human chromosomes. Preparations of human metaphase chromosomes can be prepared using standard cytogenetic techniques from human primary tissues or cell lines. Polynucleotide probes comprising at least 12 contiguous nucleotides selected from the nucleotide sequence shown in SEQ ID NO:6 are used to identify the human chromosome. The polynucleotide probes can be labeled, for example, with a radioactive, fluorescent, biotinylated, or chemiluminescent label, and detected by well known methods appropriate for the particular label selected. Protocols for hybridizing polynucleotide probes to preparations of metaphase chromosomes are also well known in the art. A polynucleotide probe will hybridize specifically to nucleotide sequences in the chromosome preparations which are complementary to the nucleotide sequence of the probe.

A polynucleotide probe which hybridizes specifically to human chromosome region 13q34 hybridizes to nucleotide sequences present in the TNFL1 gene and not to nucleotide sequences present in other human genes. A polynucleotide probe which hybridizes specifically to an TNFL1 gene provides a detection signal at least 5-, 10-, or 20-fold higher than the background hybridization provided with non-TNFL1 coding sequences.

A human chromosome which specifically hybridizes to an TNFL1 polynucleotide probe is identified as a human chromosome 13. Preferably, the polynucleotide probe identifies the long arm of human chromosome 13. More preferably, the polynucleotide probe identifies a q34 region of human chromosome 13.

The complete contents of the references cited in this disclosure are expressly incorporated by reference herein. The following examples are illustrative and are not meant to limit the scope of the invention disclosed herein.

EXAMPLE 1

This example describes cloning of the full-length cDNA for TNFL1.

TNFL1 was first identified from a database of expressed sequence tags (ESTs) by its homology to other members of the TNF family. The full-length cDNA was isolated by screening a liver cDNA library applying the genetrapper technique (Gibco). A liver library from Gibco BRL was screened using the Genetrapper cDNA positive selection system (catalog no. 10356–020) and two oligonucleotide primers. The sequence of the biotinylated primer is: 5'AGGTCCATGTCTTTGGG3' (SEQ ID NO:11) the sequence of the non biotinylated primer is: 5'GGGGAT-GAATTGAGTCTG3' (SEQ ID NO:12). The product of the repair reaction was transformed, plated on LB+ Amp (100 µg/ml) plates. The colonies were analyzed by colony hybridization with a radioactive fragment prepared by PCR using the primers 5'GTGCCCTCGAAGAAAAAG3' (SEQ ID NO:13) and 5'GCAAGTTGGAGTTCATC3' (SEQ ID NO:14).

Figure 1B:
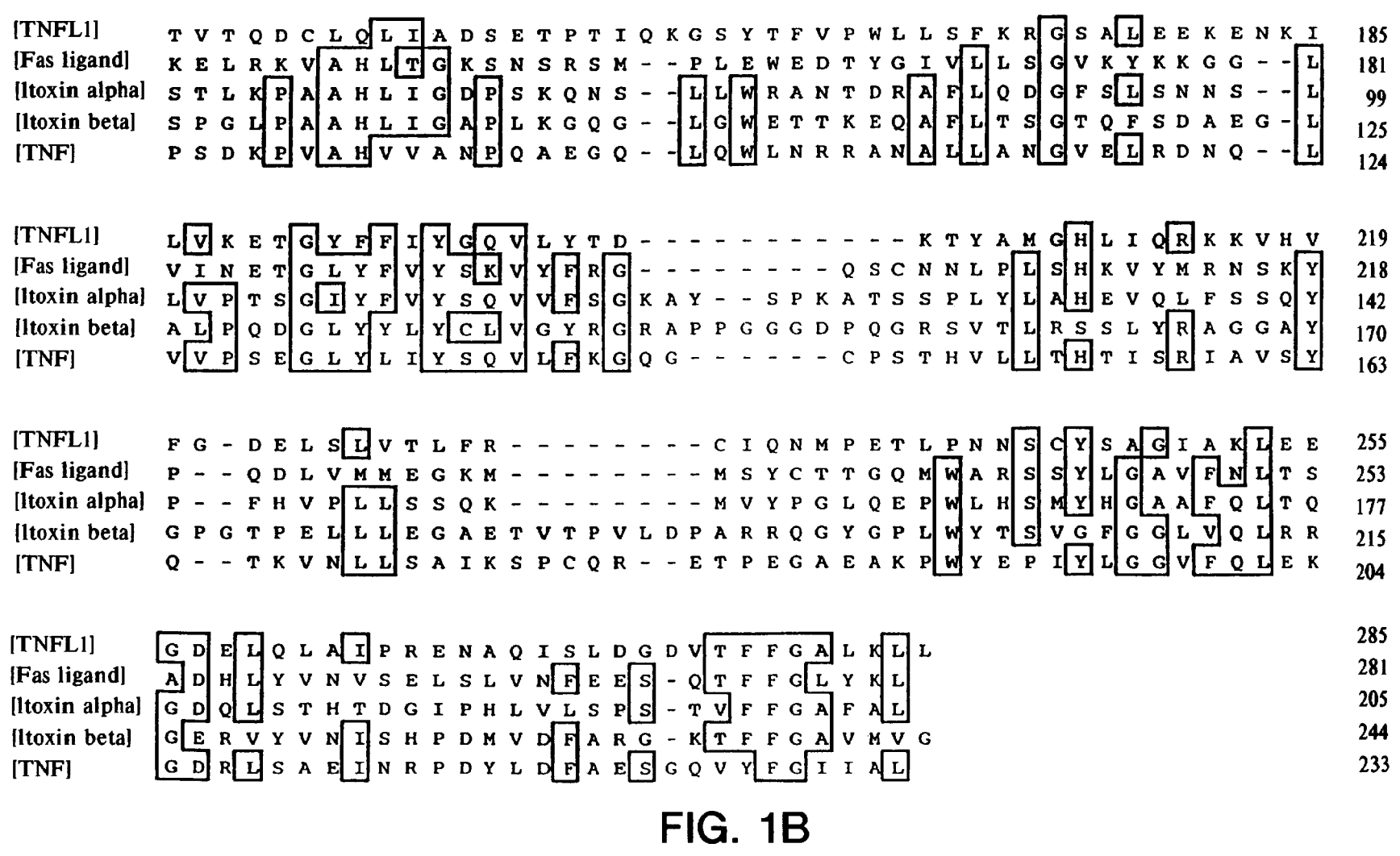

The longest open reading frame was 1280 bp long and contained a poly A tail as well as an in-fame stop codon at position −117 upstream of the ATG at position +1, suggesting that this clone was full-length. The nucleotide sequence surrounding this ATG also matched the Kozak consensus sequence. The open reading frame encodes a protein of 285 amino acids which we named Tumor Necrosis Factor Like 1 (TNFL1) (FIG. 1A) (SEQ ID NO:1).

The lack of a signal sequence at the N-terminus and the presence of an internal hydrophobic domain are indicative of a type II transmembrane structure, which is similar to the structure of most of the other members of the TNF family with the exception of lymphotoxin a. Two potential N-glycosylation sites were also identified in the extracellular region of the protein. When aligned with the extra-cellular domains from other members of the TNF family, the extracellular domain of the TNFL1 protein showed an overall homology of 28% to the proteolytically cleaved form of TNF (FIG. 1B).

EXAMPLE 2

This example shows the tissue distribution of TNFL1 mRNA.

Northern blots showing mRNAs from different tissues and cancerous cell lines were purchased from Clontech. A Northern blot with mRNAs from hematopoietic cell lines and various cell types of the immune system was prepared with 2 µg of poly A mRNA.

A probe prepared by digestion of the TNFL1 cDNA with EcoRI and XhoI was labeled by random priming with $^{35}$S and KRenow enzyme (Rediprime kit from Amersham). The hybridization was performed in the Expresshyb buffer purchased from Clontech.

A 3 kb messenger mRNA corresponding to TNFL1 mRNA was detected mainly in the organs of the immune system, such as peripheral blood lymphocytes, spleen, and thymus, as well as in the small intestine and ovary (FIG. 2A). Human TNFL1 mRNA was also detected in a few human cancer cell lines such as the chronic myelogenous leukemia cell line K562 and the melanoma cell line G361 (FIG. 2A). Mouse mRNA was detected in heart, spleen, and lung using as a probe a mouse EST sequence which is homologous to the human TNFL1 sequence (Accession No. AA254417) (FIG. 2B).

Because TNFL1 mRNA was expressed in the spleen of both mouse and human samples as well as in peripheral blood leukocytes, a more precise analysis of the protein expression levels was carried out in the same tissues.

EXAMPLE 3

This example demonstrates expression of protein levels in mouse and human tissues.

A polyclonal antibody (D2710) was raised against amino acids 234–248 of TNFL1 and purified on a protein G column followed by a peptide affinity column. Amino acids 234–248 are highly conserved between the human and the mouse protein and differ by only 4 amino acids.

Figure 3A:
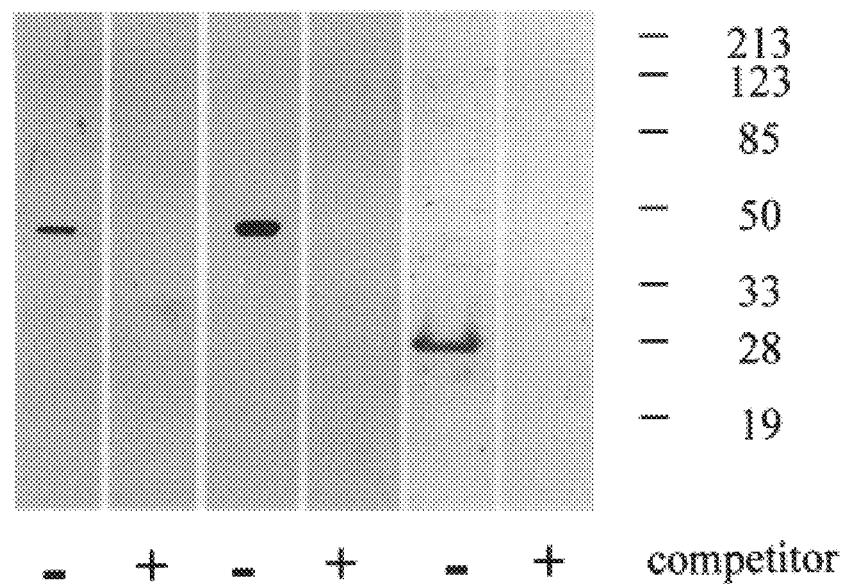
FIG. 3A shows a Western blot analysis using the affinity-purified D2710 antibody at a final concentration of 1 μg/ml. The extracts analyzed were total cell extracts of human monocytes isolated from PBMCs (lanes 1 and 2) and mouse bone marrow-derived dendritic cells (lanes 3 and 4). Lanes 5 and 6 contained 20 ng of TNFL1 protein purified from $E.$ $coli$. In lanes 2, 4, and 6 the antibody was pre-incubated with a hundred-fold molar excess of the peptide used to generate the antibody.

This antibody was able to recognize a purified 30 kDa TNFL1 protein by Western blot analysis (FIG. 3A, lane 5). A single band corresponding to a 45 kDa protein was detected in cytoplasmic extracts from mouse bone marrow-derived dendritic cells and human monocytes. Both the 30 kDa and the 45 kDa bands were absent after incubation of D2710 with an excess of competitor peptide (FIG. 3A, lanes 2, 4, and 6), suggesting that the 45 kDa protein corresponds to the full-length TNFL1 protein.

Figure 3B:
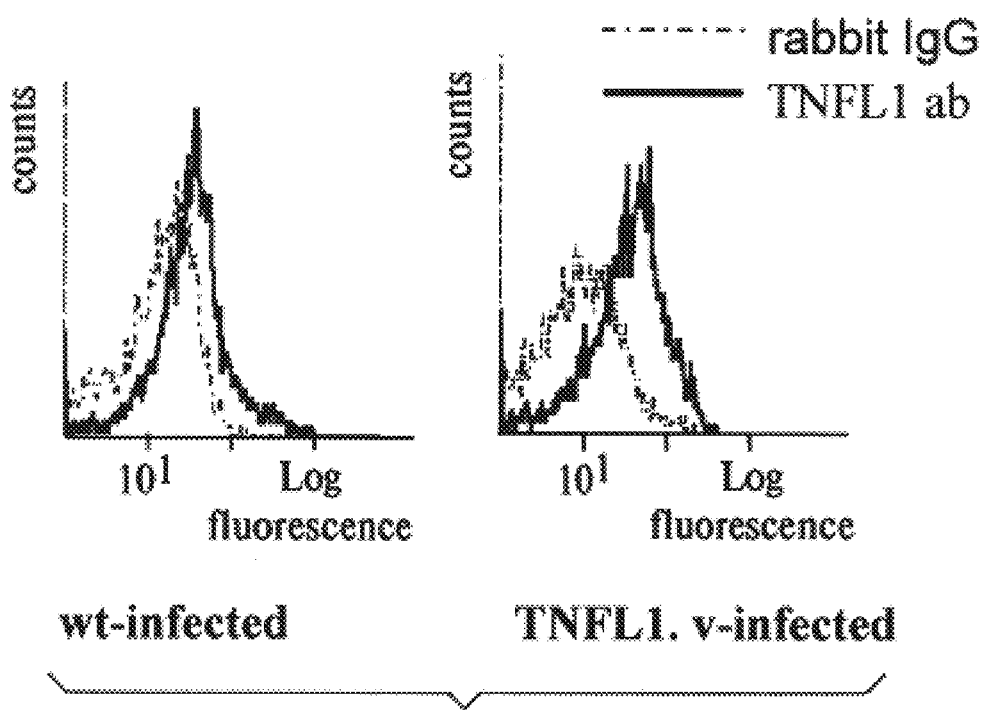
FIG. 3B shows intracellular staining of baculovirus-infected cells expressing TNFL1, using the D2710 antibody or a control rabbit antibody at a concentration of 10 μg/ml. The insect cells were fixed and permeabilized before staining and flow cytometry analysis.

The affinity purified antibody was also able to detect TNFL1 expressed in insect cells. Insect cells were infected with a recombinant baculovirus expressing the TNFL1 protein and analyzed by flow cytometry. The protein TNFL1 was detected by intracellular staining with D2710 after fixation and permneabilization of the cells infected with the recombinant virus but not the wild type virus (FIG. 3B).

Immunohistochemistry experiments were performed on sections from mouse spleen and lymphoid organs using the polyclonal antibody D2710. The spleen was isolated from an animal perfused with 4% paraformaldehyde in PBS, incubated in the same solution for one additional hour, and incubated overnight at 4° C. in a 10% sucrose solution. The spleen was then embedded in OCT prior to cryo-sectioning. The sections were stored at −80° C. Immunostaining was carried out using the following protocol. The sections were blocked in normal donkey IgG (whole molecule H+L; Jackson 017 000 003; lot 39113 at 25.5 g/l) diluted 1:100 in 1×PBS and Fc block diluted 1:50 (Pharmingen, catalog no. 01241A). The sections were then incubated with primary antibodies D2710, anti-mouse CD11c (BL3, Pharmingen, catalog no. 09702D), anti-mouse Th1.2 CD90.2 (53-2.1, Pharmingen, catalog no. 01122A), or anti-mouse CD45R/B220 (RA3-6B2, Pharmingen, catalog no. 01122A) diluted 1:50 in blocking reagent. The sections were washed three times for 3 minutes each in PBS.

The sections were then incubated in secondary antibody (biotin-labeled donkey anti-rabbit F(ab)$_2$ (Jackson 711-066-152) or biotin-labeled donkey anti-rat F(ab')$_2$ (Jackson 721-066-153) diluted 1:100 in PBS, washed 3 times for 3 min in PBS, and incubated for 30 minutes at room temperature with pre-equilibrated ABC-Alkaline Phosphatase reagent (Vector) or ABC-peroxidase (Vector). The sections were again washed 3 times for 3 minutes in PBS and incubated in a color developing reaction with levamisole (Vector; SK 5000) using a Vector black AP substrate kit (SK5200), Vector red AP substrate kit (SK 5100), or Vector AEC peroxidase substrate kit (SK4200). After washing again in PBS, alkaline phosphatase stained sections were counter-stained with hematoxylin nuclear counterstain (Vector, H3401) and methyl green (Vector; H3402). Other sections were mounted in fluoromount (Southern Biotechnology Associates, catalog no. 100–01; Fisher OB100–01).

Normal rabbit IgG (R& D Systems, catalog no. AB-105C) at a 1:50 dilution, secondary antibody at a dilution of 1:100, and secondary antibody alone at a dilution of 1:100 were used as negative controls.

Figure 3C:
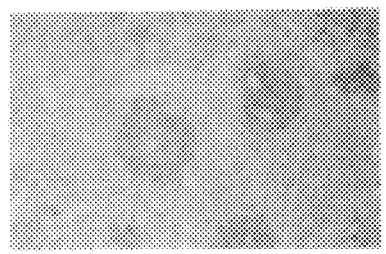
FIG. 3C shows the pattern of expression of TNFL1 in mouse spleen sections. Left panels: rabbit antibody control plus secondary antibody; right panels, anti-TNFL1 antibody plus secondary antibody. The magnification is 100× in the top panels and 200× in the bottom panels. RP, red pulp; PALS, periarteriolar lymph sheath.
Figure 3C:
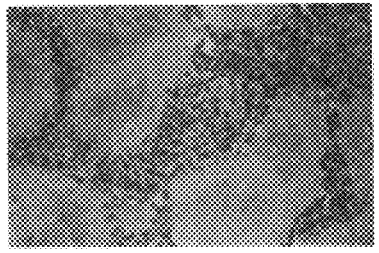
Figure 3D:
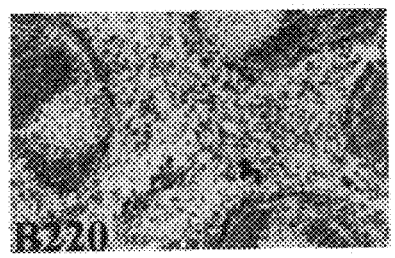
FIG. 3D shows staining of adjacent murine spleen sections for Thy-1.2, B220, TNFL1, CD11c, and Mac-3.
Figure 3D:
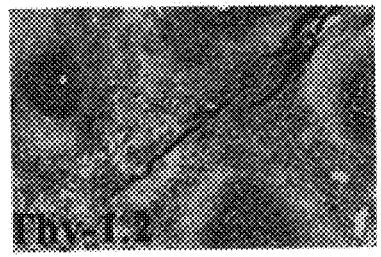
Figure 3D:
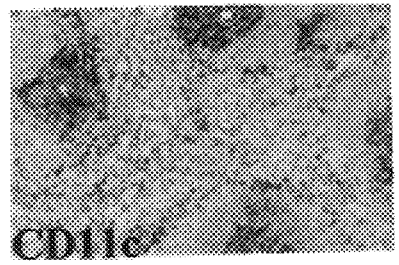
Figure 3D:
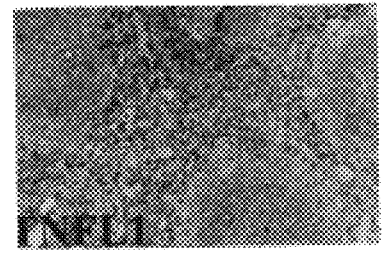
Figure 3D:
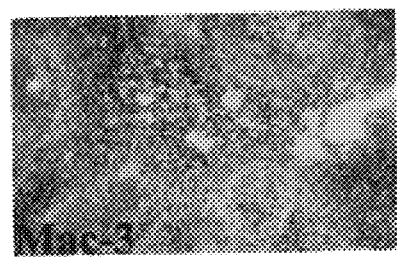

TNFL1 was constitutively and specifically expressed as a cell surfacebound protein in normal spleen (FIG. 3C), but was weakly expressed in lymph nodes, mesenteric lymph nodes, and Peyer's patches. In the spleen, the pattern of expression was restricted to the marginal zone and the red pulp. The region stained with monoclonal antibodies directed against markers of the T cell population and of the B cell zone (Th1-2 and B220 respectively) did not overlap with the region stained with the antibody specific for TNFL1 (FIG. 3D). A monoclonal antibody directed against the dendritic cell marker CD11c stained the T cell area and the marginal zone, as well as some isolated cell in the red pulp (FIG. 3D).

Although it is possible that some cell sub-types present both the CD11c antigen and the TNFL1 protein at their surface, TNFL1 does not seem to be an exclusive marker of dendritic cells in the spleen. The Mac-3 antigen, a marker for macrophages and monocytes mainly localized in the red pulp, showed a pattern of expression very similar to the one observed with TNFL1 (FIG. 3D). Overall, these results suggest that TNFL1 is expressed at the surface of splenic macrophages, monocytes, or dendritic cells usually present in the marginal zone and the red pulp.

Flow cytometry experiments were performed on human PBMCs isolated from whole blood by Ficoll gradient centrifugation and the PBMCs analyzed. TNFL1 was found to be constitutively expressed on monocytes and B cells, but not on resting CD4+ and CD8+ T cells. Mouse bone marrow-derived dendritic cells cultivated for 10 days in the presence of GM-CSF also showed some surface staining with the TNFL1 antibody (FIG. 4A). After incubation of PBMCs with anti-CD3 and anti-CD28 antibodies for 6 days in the presence of IL2, TNFL1 was shown to be upregulated at the surface of T cells (FIG. 4B).

EXAMPLE 4

This example demonstrates expression of a soluble form of TNFL1 in the periplasm of *E. coli*.

Figures 1, 2, 5A, 5B:
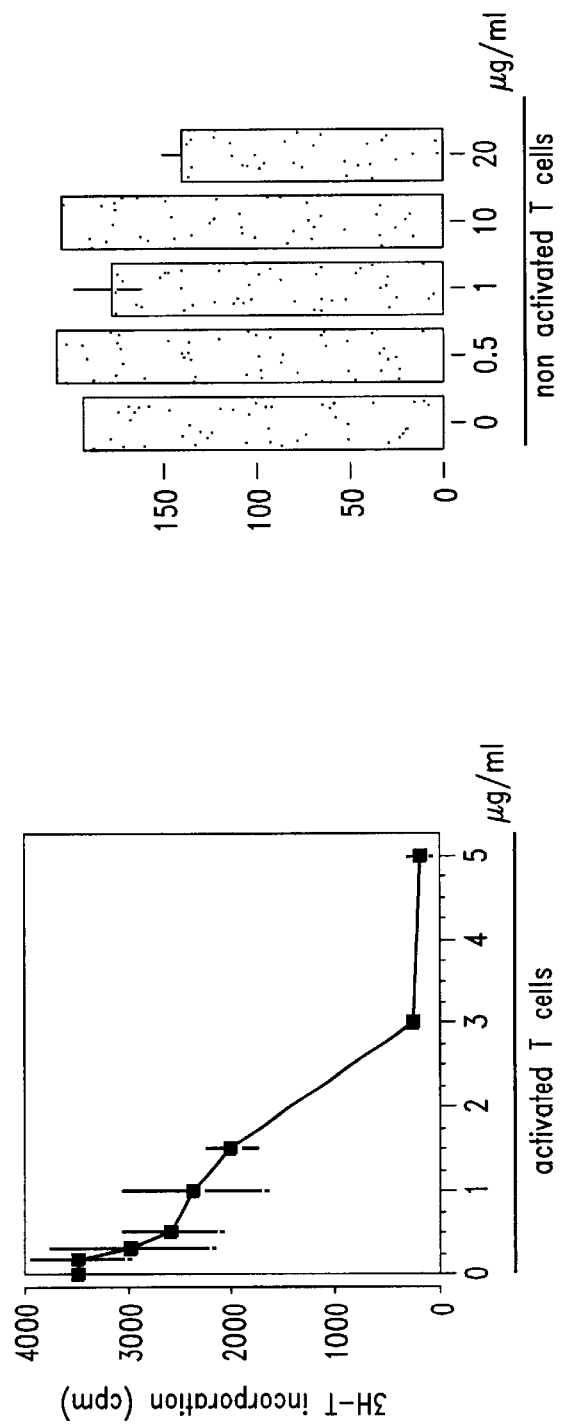
FIG. 1.
FIG. 2.
FIG. 5A shows the amino acid sequence (SEQ ID NO:2) of a soluble form of TNFL1 (sequence enclosed in brackets) which was expressed in $E.$ $coli$ as a fusion protein and used for all biological assays. The cleavage sites identified after microsequencing of the truncated form of the protein are represented as vertical bars.
FIG. 5B shows inhibition of DNA synthesis in activated but not in resting T cells by TNFL1. T cells enriched from human PBMCs were either activated with 10 μg/ml of anti-CD3 and 10 μg/ml of anti-CD28 (left panel) or untreated (right panel) for 24 hours. TNFL1 was then added at various concentrations, and $^3$H-thymidine incorporation over a period of 8 hours was measured 48 hours after addition of TNFL1.

A chimeric soluble version of TNFL1 was expressed in *E. coli* as a fusion protein comprising the extracellular portion of TNFL1 (amino acids 113–285; FIG. 5A) and the pelB signal sequence for periplasmic localization. The EYMPMD peptide (SEQ ID NO:15) was inserted between the signal sequence and the TNFL1 sequence for convenient affinity purification. The cDNA for TNFL1 was cloned into the vector pET-22b(+) from Invitrogen, which contains the pelB signal sequence for periplasmic localization. A 100 ml culture was grown at 37° C. until it reached an OD of 0.7–0.9 and then grown at 25° C. for 24 hours after induction by 1 mM IPTG. The pellet was centrifuged at 4000×g for 10 minutes and resuspended in 10 ml 30 mM Tris HCl, 20% sucrose, pH 8.0. After addition of 1 mM EDTA, the sample was incubated at room temperature for 5–10 min. The sample was then centrifuged at 8000×g at 4° C. for 10 min. The supernatant was removed, and the pellet was resuspended in 10 ml ice-cold 5 mM MgSO$_4$. After a 10 minute incubation in an icejwater bath, the sample was centrifged at 8000× g at 4° C. for 10 min. The supemnatant containing the periplasmiic fraction was stored at −80° C. in 15% glycerol. A control sample was processed in a similar way with an empty vector construct.

A similar fpasion construct was also designed for expression and purification from COS cells using the pSecTag vector (Invitrogen) with a signal sequence from the mouse Ig ê chain.

EXAMPLE 5

This example demonstrates purification of the TNFL1 fusion protein from *E. coli*.

BL21 (DE3) transformed *E. coli* were grown in a 10-1 fermenter to an OD of 29–31 before induction with IPTG. The cells were ha rvested in a Beckman J-6B centrifuge. The wet cell paste was subjected to osmotic shock treatment for periplasmic extraction (lot 10229-142) or lysozyme/EDTA spheroplast formation with retention of the spheroplast supernatant as the periplasmic fraction (lot 981001-M8). Using a Pall Filtron Centrasette tangential flow apparatus and 2 Centrasette 10 kD NMWCO membranes , the resulting periplasmic fraction was concentrated to 1 liter, then buffer-exchanged by constant-flow diafittration in the same apparatus against at least 6 volumes of PBS. The resulting solution was entrifulged at 10,000 rpm at 4° C. for 50 minutes in a Beckman J2-21 centrifuge with a JA-10 rotor.

The resulting supernatant was precipitated with 50% ammonium sulfate using an equal volume of saturated ammonium sulfate. The resulting pellet was resuspended in ¼ the original volume of PBS and loaded onto a glu-tag monoclonal antibody affinity column at a flow rate of 30 cm/hr. Following the load, a wash of 5–10 CV of PBS+0.2%

Tween 20 was performed, followed by 2 CV of PBS. Elution was effected by 5 CV of 0.1 mg/ml EYMPTD peptide (SEQ ID NO:16) (Research Genetics) followed by PBS. A strip of 1.5 CV 0.1 M glycine pH 2.7 was also collected into one-tenth volume of 1 M Tris pH 8, and the column was neutralized with 1 CV of the same.

The peptide elution was concentrated in an Amicon 8400 stirred-cell with a YM-10 membrane. Peptide removal was effected by overnight dialysis of the concentrate against PBS (except for the samples treated to remove residual detergent). Endotoxin removal was by Triton X-114 phase separation. One-ninth volume of 10% Triton X-114 protein grade (Calbiochem) was added to samples chilled on ice. Constant agitation for 30 min. at 4° C. was followed by 15 min. incubation in a 37° C. water bath. Centrifugation at 10,000× g recovered the supernatant as the detergent-poor aqueous fraction. The cycle was repeated 3–5 times, resulting in endotoxin levels of less than or equal to 0.05 EU/ml.

Detergent was removed by an anion-exchange chromatography step in which the protein was bound and eluted while the detergent and elution peptide flowed through. A Pharmacia HR 10/5 column packed with 1.7 ml TMAE-Fractogel (EM Merck) was equilibrated in 25 mM NaPi, pH 7.4, at 1 ml/minute on an Akta Explorer FPLC system. Fractions of 1 ml were collected across a 15 CV gradient from 0–0.6 M NaCl in 25 mM NaPi, pH 7.4. The protein eluted at a conductivity of about 22 mS/cm. The peak fractions were pooled and concentrated, if necessary, in a Amicon Centriplus-10 centrifugal concentration device.

The purified protein was detected in a Western blot with both the tag antibody and the D2710 antibody as a 30 kD protein (FIG. 3A). A minor additional band at 21 kD was also observed. This band was identified by microsequencing as a degradation product of the 30 kD protein (FIG. 5A).

EXAMPLE 6

This example demonstrates the effects of TNFL1 on T and B cells.

T cells isolated from healthy donors were activated for two days in the presence of anti-CD3 and anti-CD28 antibodies and incubated for an additional two days in the presence of different concentrations of purified TNFL1. Mouse and human T cells were purified by negative selection from PBMCs on a mouse or human T cell enrichment column (R&D Systems), and B cells were isolated by positive selection on Dynabeads M-450 Pan-B and detached from the beads with the polyclonal antibody Detachabead from Dynal. The T cells were activated for 2 days with anti-CD3 and anti-CD28 antibodies at a concentration of 10 µg/ml.

T cell proliferation was assessed by thymidine incorporation at day 5. The assays were performed in a 96 well plate format with 100,000 cells/well. The thymidine incorporation assay was performed by addition of $^3$H-thymidine at a concentration of 1 mCi/well. After 8 hours, the cells were harvested onto a filter-paper and $^3$H-thymidine uptake was measured by liquid scintillation counting.

The dose-response curve shows a 30-fold decrease in thymidine incorporation at the highest concentrations of TNFL1 (FIG. 5B, left). Resting T cells incubated with the ligand for two days did not show any decrease in thymidine incorporation (FIG. 5B, right).

Figure 5C:
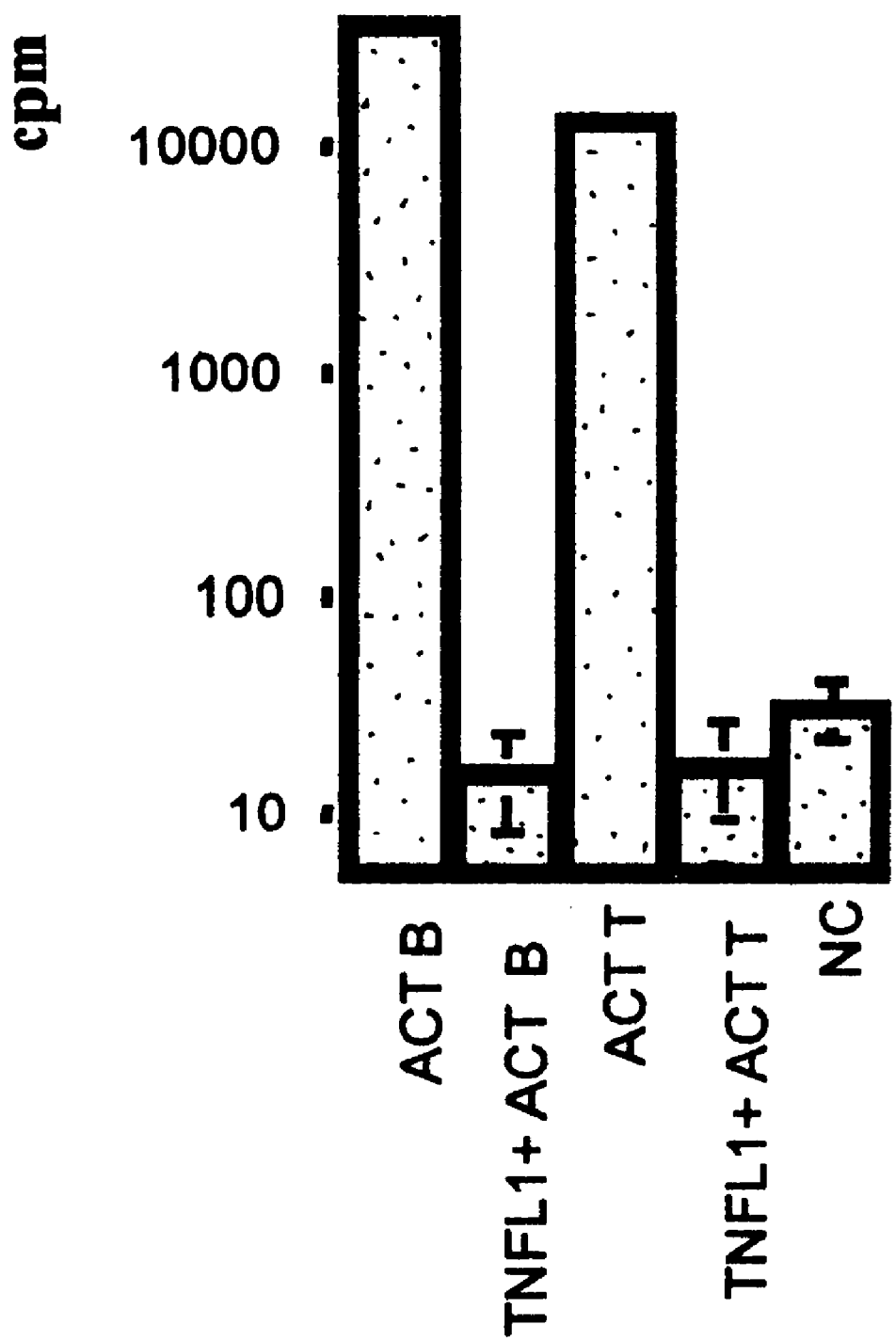
FIG. 5C shows inhibition of DNA synthesis by TNFL1 in activated B cells and activated T cells. B cells were activated with 10 μg/ml of anti-cd40 antibody. T cells were activated as described in FIG. 5B. TNFL1 was added 48 hours after activation. $^3$H-thymidine incorporation over a period of 8 hours was measured 48 hours after addition of TNFL1.

In a separate experiment, the effect of TNFL1 was tested on anti-CD3- and anti-CD28 -activated T cells and on anti-CD40-activated B cells. The T cells were activated for 2 days with anti-CD3 and anti-CD28 antibodies at a concentration of 10 µg/ml, and the B cells were activated for 2 days in the presence of anti-cd40 antibody at a concentration of 10 µg/ml. Both cell types showed a strong and comparable decrease in thymidine incorporation after addition of TNFL1 (FIG. 5C). TNFL1 also inhibited the proliferation of murine T cells activated by allogeneic bone marrow-derived DCs by 90%.

We also tested the ability of TNFL1 to decrease the proliferation rate of mouse T cells activated by allogeneic bone marrow-derived dendritic cells in a mixed lymphocyte reaction LR). For the MLR reaction, 100,000 mouse T cells were mixed with 10,000 mouse dendritic cells. Dendritic cells were prepared from red blood cell-depleted bone marrow cells. The cells were resuspended in culture medium in a bacterial Petri dish at a concentration of $0.2 \times 10^6$ cells per ml. Recombinant mouse GM-CSF was added to the cells at a final concentration of 200 U/ml on days 1, 2, 3, 6 and 8. On day 10, LPS at 1 µg/ml or TNF-α at 500 U/ml was added to the cells. The cells were harvested on day 11.

In the absence of TNFL1, the cultured DCs triggered a 100-fold increase in thymidine incorporation in the responding T cells. When the assay was performed in the presence of TNFL1, the increase in thymidine incorporation was only 10-fold, showing that TNFL1 is able to reduce the T cell stimulation induced by allogeneic antigen presenting cells.

Overall, these results indicate that TNFL1 is able to induce a decrease in thymidine incorporation in activated B and T cells. This effect could be due to a direct inhibition of proliferation or to the induction of apoptosis of B and T cells.

In order to elucidate the exact mechanism of action of TNFL1 on activated T cells, a 0.1% sodium citrate. TUNEL staining was performed with 50 µl of TUNEL mix per sample at 37° C. for 1 hour. Negative controls were treated similarly but were not exposed to the enzyme.

Figures 1, 5D:
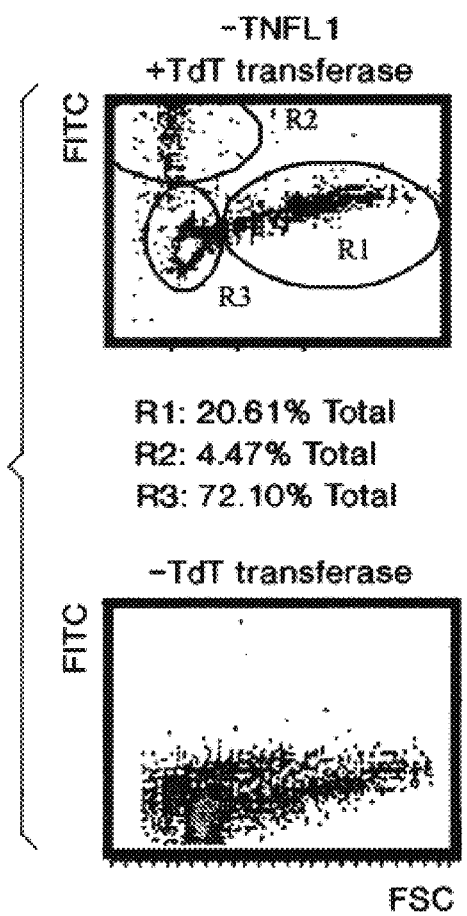
FIG. 5D shows that TNFL1 induces apoptosis of activated T cells. T cells were activated with anti-CD3 and anti-CD28 for 48 hours. TNFL1 was added at 2 μg/ml and incubated for an additional 48 hours. Apoptosis was assessed by TUNEL assay. (R1), blasting cells; (R2), apoptotic cells; (R3), resting non-apoptotic cells.
Figures 2, 5D:
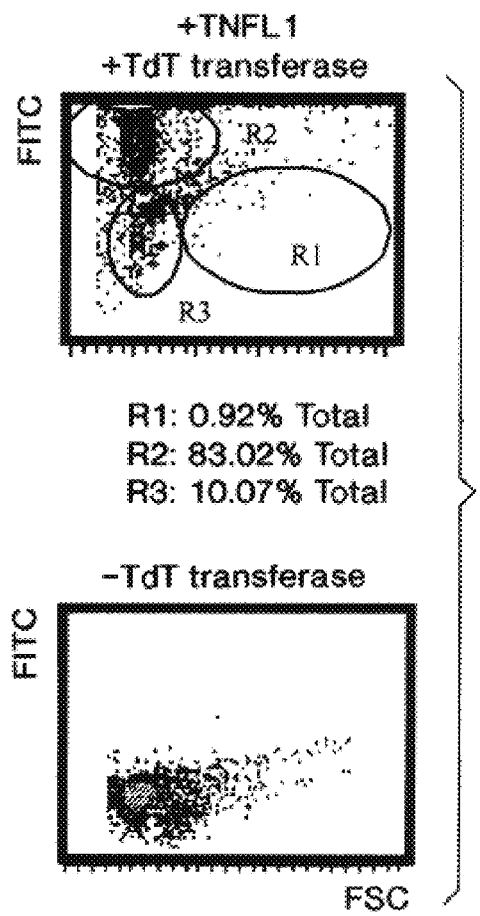

After incubation of the T cells with TNFL1, the amount of apoptotic cells measured by flow cytometry analysis (FIG. 5D). The blasted cells, visualized by forward size scattering (region R1), almost totally disappeared after addition of TNFL1. At the same time, the amount of apoptotic, FITC-positive cells (region R2) dramatically increased. No apoptotic cells were detected in the absence of dUTP-FITC, whether or not TNFL1 was added.

These results strongly suggest that TNFL1 is able to induce apoptotic cell death of blasting as well as of slightly activated T cells.

EXAMPLE 7

This example demonstrates that TNFL1 activates NFκB and leads to its translocation to the nucleus.

TNF activates the transcription factor NFκB. NFκB represents a family of related proteins involved in the transcriptional control of numerous cellular genes such as interleukin-2, interleukin-2 receptor, β-interferon, granulocyte macrophage colony-stimulating factor, histocompatibility antigens, TNF, and lymphotoxin a. We therefore decided to test whether TNFL1 could induce a similar intracellular response in Jurkat cells.

Jurkat cells ($10^7$) were incubated for one hour with PMA at a concentration of 1 µg/ml or TNFL1 at a concentration of 3 µg/ml in 1 ml of RPMI and 10% FBS. Nuclear extracts were prepared by centrifuging the cells at 2000 rpm and resuspending the pellet in 1 ml of cold buffer A (10 mM Hepes, 1.5 mM MgCl$_2$, 10 mM KCl, 0.5 mM DTT, 0.5 mM PMSF). After a second centrifugation at 2000 rpm, the pellet was resuspended in 20 µl of buffer A and 0.1% NP40, incubated for 10 minutes on ice, and then centrifuged. The pellet was resuspended in 15 µl of buffer C (20 mM Hepes, pH 7.9, 0.42 M NaCl, 1.5 mM MgCl$_2$, 0.2 mM EDTA, pH 7.4, 25% glycerol, 0.5 mM PMSF, 0.5 mM DTT, 50 µg/ml leupeptin, 50 µg/ml pepstatin, and 78 µg/ml benzamidin). The mixture was incubated for 15 minutes on ice, then centrifuged for 10 minutes at 14,000 rpm at 4° C. The supernatant was diluted in 75 µl of buffer D (20 mM Hepes, pH 7.9, 20% glycerol, 0.2 mM EDTA, pH 7.4, 50 mM KCl, 0.5 nM DTT, and 0.5 mM PMSF).

Five µg of nuclear extract was incubated for 10 minutes at 4° C. in the presence of 5 µg of polydIdc and wild-type or mutated competitor oligonucleotide (2 ng to 200 ng). Two-tenths of a nanogram of polynucleotide kinase-radiolabeled probe was added to the reaction, and the mixture was incubated at room temperature for 30 min.

Figure 5E:
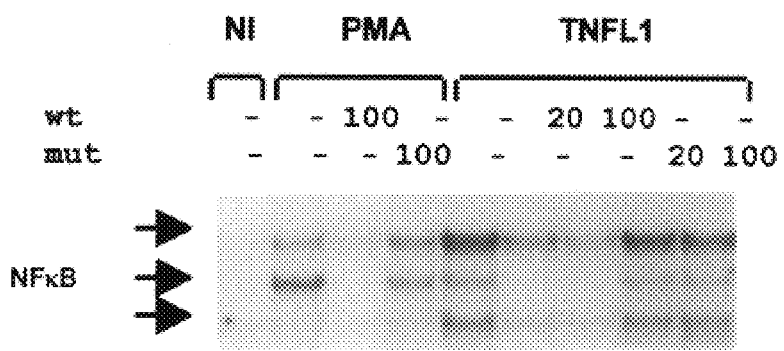
FIG. 5E shows that TNFL1 induces NFκB activation in Jurkat cells. An electrophoretic mobility shift assay was performed with an NFκB probe on nuclear cell extracts prepared from Jurkat cells treated with PMA (1 μg/ml) or TNFL1 (3 μg/ml) for one hour. Wild-type (wt, 20 ng) and mutated (mut, 100 ng) non-radiolabeled oligonucleotides were used as competitors in the reaction.

The mixture was loaded on a 5% acrylamide 60:1×linked gel in Tris-glycine buffer, pH 8.3, and analyzed in an electrophoretic mobility shift assay. Specific bands, identified by competition with wild-type or mutated NFκB binding sites, were observed with both PMA- and TNFL1-treated extracts (FIG. 5E), indicating that TNFL1 is indeed able to activate NFκB and leads to its translocation to the nucleus.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide which is at least 90% identical to the full length nucleotide sequence of SEQ ID NO:6, and encodes a protein selected from the group consisting of a protein having the amino acid sequence of SEQ ID NO:1, and a protein which indices activation of NfκB and induces apoptosis of activated T cells.

2. The polynucleotide of claim 1, wherein said polynucleotide is at least 96% identical to the nucleotide sequence of SEQ ID NO:6.

3. The polynucleotide of claim 1, wherein said polynucleotide is at least 97% identical to the nucleotide sequence of SEQ ID NO:6.

4. The polynucleotide of claim 1, wherein said polynucleotide is at least 98% identical to the nucleotide sequence of SEQ ID NO:6.

5. The polynucleotide of claim 1, wherein said polynucleotide is at least 99% identical to the nucleotide sequence of SEQ ID NO:6.

6. An isolated polynucleotide comprising the nucleotide sequence of SEQ ID NO:6.

* * * * *